(12) United States Patent
Lehmann

(10) Patent No.: US 6,579,975 B1
(45) Date of Patent: Jun. 17, 2003

(54) CONSENSUS PHYTASES

(75) Inventor: Martin Lehmann, Inzlingen (DE)

(73) Assignee: Roche Vitamins, Inc., Parsippany, NJ (US)

( * ) Notice: Subject to any disclaimer, the term of this patent is extended or adjusted under 35 U.S.C. 154(b) by 386 days.

(21) Appl. No.: 09/634,493

(22) Filed: Aug. 8, 2000

Related U.S. Application Data

(62) Division of application No. 09/121,425, filed on Jul. 23, 1998, now Pat. No. 6,153,418.

(30) Foreign Application Priority Data

Jul. 24, 1997 (EP) .............................. 97112688

(51) Int. Cl.[7] .............................. C12N 9/16; C12N 5/10; C12N 15/79; C07H 21/04; C12P 21/00
(52) U.S. Cl. .................. 536/23.2; 435/69.1; 435/320.1; 435/325; 435/252.3; 435/195; 435/196
(58) Field of Search ........................ 536/23.2; 435/69.1, 435/320.1, 325, 252.3, 196, 195

(56) References Cited

U.S. PATENT DOCUMENTS

| | | | |
|---|---|---|---|
| 5,436,156 A | 7/1995 | Van Gorcom et al. | ... 435/252.3 |
| 5,443,979 A | 8/1995 | Van Loon et al. | .......... 435/195 |
| 5,863,533 A | 1/1999 | Van Gorcom et al. | ..... 424/94.6 |
| 6,291,221 B1 | 9/2001 | Van Loon et al. | .......... 435/196 |
| 6,358,722 B1 | 3/2002 | Van Loon et al. | .......... 435/196 |
| 6,391,605 B1 | 5/2002 | Kostrewa et al. | ........... 435/196 |

FOREIGN PATENT DOCUMENTS

| | | |
|---|---|---|
| DE | 1 492 060 | 3/1969 |
| EP | 0 035 204 A2 | 9/1981 |
| EP | 420 358 | 4/1991 |
| EP | 0 422 697 A1 | 4/1991 |
| EP | 299 108 | 5/1994 |
| EP | 0 619 369 | 10/1994 |
| EP | 684 313 | 11/1995 |
| EP | 747 483 | 12/1996 |
| EP | 0 758 018 A1 | 2/1997 |
| EP | 0 897 010 A2 | 2/1999 |
| EP | 0 897 985 A2 | 2/1999 |
| NZ | 235 478 | 9/1990 |
| WO | WO 91/14773 | 10/1991 |
| WO | WO 93/16175 | 8/1993 |
| WO | WO 94/03072 | 2/1994 |
| WO | WO 94/03612 | 2/1994 |
| WO | WO 95/00662 | 1/1995 |
| WO | WO 98/54980 | 12/1998 |

OTHER PUBLICATIONS

Pasamontes et al., Appl. Environ. Microbiol. 63:1696–1700, 1997.*
Pasamontes et al., EMBL accession No. O00092, Jul. 1, 1997.*
U.S. patent application Ser. No. 08/938,954, Van Loon et al., filed Jun. 3, 1997.
Shieh and Ware, *Appl. Microbiol.* vol. 16, pp. 1348–1351 (1968).
Janecek, S., *Process Biochem.*, _vol. 28, pp. 435–445 (1993).
Fersht, A.R. and Serrano, L., *Curr. Opin. Struct. Biol.*, vol. 3, pp. 75–83 (1993).
Alber, T., *Annu. Rev. Biochem.*, vol. 58, pp. 765–798 (1989).
Matthews, B.W., *Biochemistry*, vol. 26, pp. 6885–6888 (1987).
Matthews, B.W., *Curr. Opin. Struct. Biol.*, vol. 1, pp. 17–21 (1991).
Pen, et al., *Bio/Technology*, vol. 11, pp. 811–814 (1994).
Stuber, et al., *Immunological Methods*, eds. Lefkovits and Pernis, Academic Press Inc., vol. IV, pp. 121–152 (1990).
Serrano, L. et al., *J. Mol. Biol.*, vol. 223, pp. 305–312 (1993).
Steipe, B., et al., J. Mol. Biol., vol., 240, pp. 188–192 (1994).
Dox, et al., *J. Biol. Chem.*, vol. 10, pp. 183–186 (1911).
Howson, et al., *Enzyme Microb. Technol.*, vol. 5, pp. 377–382 (1983).
Lambrechts, et al., *Biotech. Lett.*, vol. 14, No. 1, pp. 61–66 (1992).
Van Hartingsveldt, et al., *Gene*, vol. 127, pp. 87–94 (1993).
Piddington, et al., *Gene*, vol. 133, pp. 55–62 (1993).
Kraulis, P.J., *Appl. Cryst.*, vol. 24, pp. 946–950 (1991).
Merrit, et al., *Acta Cryst.*, pp. 869–873 (1994).
Wodzinzki, et al., *Advances in Applied Microbiology*, vol. 42, pp. 263–303 (1996).
Mitchell, et al., *Microbiology*, vol. 143, pp. 245–252 (1997).
Kostrewa, et al., *Nature Structural Biology*, vol. 4, pp. 185–190 (1997).
Simons, et al., *Br. J. Nutr.*, vol. 64, pp. 525–540 (1990).
Schoner, et al., *J. Anim. Physiol. a. Anim. Nutr.*, vol. 66, pp. 248–255 (1991).
Jongbloed, et al., *J. Anim. Sci.*, vol. 70, pp. 1159–1168 (1992).
Perney, et al., *Poultry Sci.*, vol. 72, pp. 2106–2114 (1993).
Farrell, et al., *J. Anim. Physiol. a. Anim. Nutr.*, vol. 69, pp. 278–283 (1993).
Broz, et al., *Br. Poultry Sci.*, vol. 35, pp. 273–280 (1994).
Dungelhoef, et al., *Animal Feed Sci. Technol.*, vol. 49, pp. 1–10 (1994).
Piccotti, et al., *J. Immunol.*, pp. 643–648 (1997).
Presentation by Dr. Luis Pasamontes at the Institute of Med. Microbiologie, Basel, Switzerland, Feb. 11, 1997.
Mullaney, et al., *Appl. Microbiol Biotechnol.*, vol. 35, pp. 611–614 (1991).

(List continued on next page.)

*Primary Examiner*—Rebecca E. Prouty
*Assistant Examiner*—Delia Ramirez
(74) *Attorney, Agent, or Firm*—Bryan Cave LLP

(57) ABSTRACT

A process for obtaining a consensus protein from a group of amino acid sequences of a defined protein family, proteins and polynucleotides so obtained, and compositions containing such proteins.

5 Claims, 25 Drawing Sheets

OTHER PUBLICATIONS

Conneely, O.M., *Biotechnology in the Feed Industry*, T.P. Lyons (ed.), Alltech Technical Publications, pp. 57–66 (1992).

R.F. Doolittle., et al., *The Proteins*, Neurath, et al. editors, Academic Press, New York, pp. 14 (1979).

Nunes, C.S., *Biol. Abstr.*, vol. 98 Ref. No. 126045 (1994).

Segueilha, et al., *J. Fermentation and Bioeng.*, vol. 74 (1), pp. 7–11 (1992).

Suzuki, et al., *Bull. Coll. Agr.*, Tokyo Imp. Univ., vol. 7, pp. 495 (1907).

Yamada, et al., *Agr. Biol. Chem.*, vol. 32, pp. 1275–1282 (1968).

Lee, C., et al., *Science*, vol. 239, pp. 1288–1291 (1988).

Yamamoto, et al., *Agr. Biol. Chem.* vol. 36 (12), pp. 2097–2103 (1972).

Ullah, et al., "Identification of Active–Site Residues in *Aspergillus ficuum* Extracellular pH 2.5 Optimum Acid Phosphatase," *Biochemical and Biophysical Research Communications*, vol. 192, No. 2, pp. 754–759 (1993).

Khare, et al., "Entrapment of Wheat Phytase in Polyacrylamide Gel and its Application in Soymilk Phytase Hydrolysis," *Biotechnol. Appl. Biochem.* vol. 19, pp. 193–198 (1994).

Derwent English language abstract of DE 1 492 060 (document B15) (1969).

Derwent accession No. XP–002120048, English language abstract of JP 09065877 (1997).

* cited by examiner

```
                                1
50
A. terreus 9A-1          KhsDCNSVDh GYQCFPELSH kWGlYAPYFS LQDESPFPlD
VPEDChITFV
A. terreus cbs           NhsDCTSVDr GYQCFPELSH kWGlYAPYFS LQDESPFPlD
VPDDChITFV
A. niger var. awamori    NqsTCDTVDQ GYQCFSETSH LWGQYAPFFS LANESAISPD
VPAGCrVTFA
A. niger T213            NqsSCDTVDQ GYQCFSETSH LWGQYAPFFS LANESVISPD
VPAGCrVTFA
A. niger NRRL3135        NqsSCDTVDQ GYQCFSETSH LWGQYAPFFS LANESVISPE
VPAGCrVTFA
A. fumigatus 13073       GSkSCDTVDl GYQCsPATSH LWGQYSPFFS LEDElSVSSK
LPKDCrITLV
A. fumigatus 32722       GSkSCDTVDl GYQCsPATSH LWGQYSPFFS LEDElSVSSK
LPKDCrITLV
A. fumigatus 58128       GSkSCDTVDl GYQCsPATSH LWGQYSPFFS LEDElSVSSK
LPKDCrITLV
A. fumigatus 26906       GSkSCDTVDl GYQCsPATSH LWGQYSPFFS LEDElSVSSK
LPKDCrITLV
A. fumigatus 32239       GSkACDTVEl GYQCsPGTSH LWGQYSPFFS LEDElSVSSD
LPKDCrVTFV
A. nidulans              QNHSCNTADG GYQCFPNVSH VWGQYSPYFS IEQESAISeD
VPHGCeVTFV
T. thermophilus          DSHSCNTVEG GYQCrPEISH sWGQYSPFFS LADQSEISPD
VPQNCkITFV
M. thermophila           ESRPCDTpDl GFQCgTAISH FWGQYSPYFS VpSElDaS..
IPDDCeVTFA
```

FIG. 1A

```
Consensus              NSHSCDTVDG GYQCFPEISH LWGQYSPYFS LEDESAISPD
VPDDC-VTFV Consensus phytase      NSHSCDTVDG GYQCFPEISH LWGQYSPYFS LEDESAISPD
VPDDCRVTFV 51
100
A. terreus 9A-1        QVLARHGARs PThSKtKAYA AtIAAIQKSA TaFpGKYAFL
QSYNYSLDSE
A. terreus cbs         QVLARHGARs PTDSKtKAYA AtIAAIQKNA TaLpGKYAFL
KSYNYSMGSE
A. niger var. awamori  QVLSRHGARY PTESKgKkYS ALIEEIQQNV TtFDGKYAFL
KTYNYSLGAD
A. niger T213          QVLSRHGARY PTESKgKkYS ALIEEIQQNV TtFDGKYAFL
KTYNYSLGAD
A. niger NRRL3135      QVLSRHGARY PTDSKgKkYS ALIEEIQQNA TtFDGKYAFL
KTYNYSLGAD
A. fumigatus 13073     QVLSRHGARY PTSSKsKkYK kLVTAIQaNA TdFKGKFAFL
KTYNYTLGAD
A. fumigatus 32722     QVLSRHGARY PTSSKsKkYK kLVTAIQaNA TdFKGKFAFL
KTYNYTLGAD
A. fumigatus 58128     QVLSRHGARY PTSSKsKkYK kLVTAIQaNA TdFKGKFAFL
KTYNYTLGAD
A. fumigatus 26906     QVLSRHGARY PTSSKsKkYK kLVTAIQaNA TdFKGKFAFL
KTYNYTLGAD
A. fumigatus 32239     QVLSRHGARY PTASKsKkYK kLVTAIQKNA TeFKGKFAFL
ETYNYTLGAD
```

FIG. 1B

| | |
|---|---|
| *A. nidulans* | QVLSRHGARY PTESKsKAYS GLIEAIQKNA TsFwGQYAFL ESYNYTLGAD |
| *T. thermophilus* | QLLSRHGARY PTSSKtElYS QLISrIQKTA TaYKGyYAFL KDYrYqLGAN |
| *M. thermophila* | QVLSRHGARa PTlKRaaSYv DLIDrIHhGA IsYgPgYEFL RTYDYTLGAD |
| | |
| Consensus | QVLSRHGARY PTSSK-KAYS ALIEAIQKNA T-FKGKYAFL KTYNYTLGAD |
| Consensus phytase | QVLSRHGARY PTSSKSKAYS ALIEAIQKNA TAFKGKYAFL KTYNYTLGAD |

101

150

| | |
|---|---|
| *A. terreus* 9A-1 | ELTPFGrNQL rDlGaQFYeR YNALTRhInP FVRATDASRV hESAEKFVEG |
| *A. terreus* cbs | NLTPFGrNQL qDlGaQFYRR YDTLTRhInP FVRAADSSRV hESAEKFVEG |
| *A. niger* var. *awamori* | DLTPFGEQEL VNSGIKFYQR YESLTRNIIP FIRSSGSSRV IASGEKFIEG |
| *A. niger* T213 | DLTPFGEQEL VNSGIKFYQR YESLTRNIIP FIRSSGSSRV IASGEKFIEG |
| *A. niger* NRRL3135 | DLTPFGEQEL VNSGIKFYQR YESLTRNIVP FIRSSGSSRV IASGKKFIEG |
| *A. fumigatus* 13073 | DLTPFGEQQL VNSGIKFYQR YKALARSVVP FIRASGSDRV IASGEKFIEG |
| *A. fumigatus* 32722 | DLTPFGEQQL VNSGIKFYQR YKALARSVVP FIRASGSDRV IASGEKFIEG |

FIG. 1C

```
A. fumigatus 58128    DLTPFGEQQL VNSGIKFYQR YKALARSVVP FIRASGSDRV
IASGEKFIEG
A. fumigatus 26906    DLTAFGEQQL VNSGIKFYQR YKALARSVVP FIRASGSDRV
IASGEKFIEG
A. fumigatus 32239    DLTPFGEQQM VNSGIKFYQK YKALAgSVVP FIRSSGSDRV
IASGEKFIEG
A. nidulans           DLTiFGENQM VDSGaKFYRR YKNLARKnTP FIRASGSDRV
VASAEKFING
T. thermophilus       DLTPFGENQM IQlGIKFYnH YKSLARNaVP FVRCSGSDRV
IASGrlFIEG
M. thermophila        ELTRtGQQQM VNSGIKFYRR YRALARKsIP FVRTAGqDRV
VhSAENFTQG Consensus             DLTPFGENQM VNSGIKFYRR YKALARK-VP FVRASGSDRV
IASAEKFIEG
Consensus phytase     DLTPFGENQM VNSGIKFYRR YKALARKIVP FIRASGSDRV
IASAEKFIEGAA
```

FIG. 1D 151
200
A. terreus 9A-1            FQTARqDDHh ANpHQPSPrV DVaIPEGSAY NNTLEHSlCT AFES...STV
A. terreus cbs             FQNARqGDPh ANpHQPSPrV DVVIPEGTAY NNTLEHSICT AFEA...STV
A. niger var. awamori      FQSTKLkDPr AqpgQSSPkI DVVISEASSs NNTLDPGTCT VFED...SEL
A. niger T213              FQSTKLkDPr AqpgQSSPkI DVVISEASSs NNTLDPGTCT VFED...SEL
A. niger NRRL3135          FQSTKLkDPr AqpgQSSPkI DVVISEASSs NNTLDPGTCT VFED...SEL
A. fumigatus 13073         FQqAKLADPG A.TNRAAPAI SVIIPESETF NNTLDHGVCT kFEA...SQL
A. fumigatus 32722         FQqAKLADPG A.TNRAAPAI SVIIPESETF NNTLDHGVCT kFEA...SQL
A. fumigatus 58128         FQqAKLADPG A.TNRAAPAI SVIIPESETF NNTLDHGVCT kFEA...SQL
A. fumigatus 26906         FQqAKLADPG A.TNRAAPAI SVIIPESETF NNTLDHGVCT kFEA...SQL
A. fumigatus 32239         FQqANVADPG A.TNRAAPVI SVIIPESETY NNTLDHSVCT NFEA...SEL
A. nidulans                FRKAQLhDHG S..gQATPVV NVIIPEiDGF NNTLDHSTCV SFEN...DEr
T. thermophilus            FQSAKVlDPh SDkHDAPPTI NVIIeEGPSY NNTLDtGSCP VFED...SSg
M. thermophila             FHSAlLADRG STvRPTlPyd mVVIPETAGa NNTLHNDlCT AFEEgpySTI

FIG. 1E

```
Consensus                 FQSAKLADPG S-PHQASPVI NVIIPEGSGY NNTLDHGTCT
AFED---SEL Consensus phytase         FQSAKLADPG SQPHQASPVI DVIIPEGSGY NNTLDHGTCT
AFED...SEL 201                                              250
A. terreus 9A-1           GDDAvANFTA VFAPAIaQRL EADLPGVqLS TDDVVnLMAM
CPFETVSlTD A. terreus cbs            GDAAADNFTA VFAPAIakRL EADLPGVqLS ADDVVnLMAM
CPFETVSlTD A. niger var. awamori     ADTVEANFTA TFAPSIRQRL ENDLSGVTLT DTEVTyLMDM
CSFDTIStST A. niger T213             ADTVEANFTA TFAPSIRQRL ENDLSGVTLT DTEVTyLMDM
CSFDTIStST A. niger NRRL3135         ADTVEANFTA TFVPSIRQRL ENDLSGVTLT DTEVTyLMDM
CSFDTIStST A. fumigatus 13073        GDEVAANFTA lFAPDIRARa EkHLPGVTLT DEDVVsLMDM
CSFDTVARTS A. fumigatus 32722        GDEVAANFTA lFAPDIRARa EkHLPGVTLT DEDVVsLMDM
CSFDTVARTS A. fumigatus 58128        GDEVAANFTA lFAPDIRARa EkHLPGVTLT DEDVVsLMDM
CSFDTVARTS A. fumigatus 26906        GDEVAANFTA lFAPDIRARa KkHLPGVTLT DEDVVsLMDM
CSFDTVARTS A. fumigatus 32239        GDEVEANFTA lFAPAIRARI EkHLPGVqLT DDDVVsLMDM
CSFDTVARTA
```

FIG. 1F

| | | | | |
|---|---|---|---|---|
| A. nidulans CSFDTMARTA | ADEiEANFTA | IMGPPIRkRL | ENDLPGIKLT | NENVIyLMDM |
| T. thermophilus CPFETLARNh | GHDAQEKFAk | qFAPAIlEKI | KDHLPGVDLA | vSDVpyLMDL |
| M. thermophila CPFETVAsSS | GDDAQDTYlS | TFAGPItARV | NANLPGANLT | DADTVaLMDL |
| Consensus CPFETVARTS | GDDAEANFTA | TFAPAIRARL | EADLPGVTLT | DEDVV-LMDM |
| Consensus phytase CPFETVARTS | GDDVEANFTA | LFAPAIRARL | EADLPGVTLT | DEDVVYLMDM |

```
                    251                                        300
```

| | | | | |
|---|---|---|---|---|
| A. terreus 9A-1 YGYGGGNPLG | ........ | ...DAhTLSPFC | DLFTAtEWtq | YNYLlSLDKY |
| A. terreus cbs YGYGGGNPLG | ........ | ...DAhTLSPFC | DLFTAaEWtq | YNYLlSLDKY |
| A. niger var. awamori YGHGAGNPLG | ........ | ...vDTKLSPFC | DLFTHdEWih | YDYLQSLkKY |
| A. niger T213 YGHGAGNPLG | ........ | ...vDTKLSPFC | DLFTHdEWih | YDYLRSLkKY |
| A. niger NRRL3135 YGHGAGNPLG | ........ | ...vDTKLSPFC | DLFTHdEWin | YDYLQSLkKY |
| A. fumigatus 13073 YGYGAGNPLG | ........ | ...DASQLSPFC | QLFTHnEWkk | YNYLQSLGKY |
| A. fumigatus 32722 YGYGAGNPLG | ........ | ...DASQLSPFC | QLFTHnEWkk | YNYLQSLGKY |

FIG. 1G

```
A. fumigatus 58128      ........ ...DASQLSPFC QLFTHnEWkk YNYLQSLGKY
YGYGAGNPLG
A. fumigatus 26906      ........ ...DASQLSPFC QLFTHnEWkk YNYLQSLGKY
YGYGAGNPLG
A. fumigatus 32239      ........ ...DASELSPFC AIFTHnEWkk YDYLQSLGKY
YGYGAGNPLG
A. nidulans             ........ ...HGTELSPFC AIFTEkEWlq YDYLQSLSKY
YGYGAGSPLG
T. thermophilus         ........ ...TDT.LSPFC ALsTQeEWqa YDYYQSLGKY
YGnGGGNPLG
M. thermophila          sdpatadagg gNGrpLSPFC rLFSEsEWra YDYLQSVGKW
YGYGPGNPLG Consensus               ---------- -DATELSPFC ALFTE-EW-- YDYLQSLGKY
YGYGAGNPLG
Consensus phytase       .......... .DATELSPFC ALFTHDEWRQ YDYLQSLGKY
YGYGAGNPLG
```

FIG. 1H

```
                            301
350
A. terreus 9A-1         PVQGVGWaNE LMARLTRAPV HDHTCVNNTL DASPATFPLN
ATLYADFSHD A. terreus cbs          PVQGVGWaNE LIARLTRSPV HDHTCVNNTL DANPATFPLN
ATLYADFSHD A. niger var. awamori   PTQGVGYaNE LIARLTHSPV HDDTSSNHTL DSNPATFPLN
STLYADFSHD A. niger T213           PTQGVGYaNE LIARLTHSPV HDDTSSNHTL DSNPATFPLN
STLYADFSHD A. niger NRRL3135       PTQGVGYaNE LIARLTHSPV HDDTSSNHTL DSSPATFPLN
STLYADFSHD A. fumigatus 13073      PAQGIGFtNE LIARLTRSPV QDHTSTNsTL vSNPATFPLN
ATMYVDFSHD A. fumigatus 32722      PAQGIGFtNE LIARLTRSPV QDHTSTNsTL vSNPATFPLN
ATMYVDFSHD A. fumigatus 58128      PAQGIGFtNE LIARLTRSPV QDHTSTNsTL vSNPATFPLN
ATMYVDFSHD A. fumigatus 26906      PAQGIGFtNE LIARLTRSPV QDHTSTNsTL vSNPATFPLN
ATMYVDFSHD A. fumigatus 32239      PAQGIGFtNE LIARLTNSPV QDHTSTNsTL DSDPATFPLN
ATIYVDFSHD A. nidulans             PAQGIGFtNE LIARLTQSPV QDNTSTNHTL DSNPATFPLD
rKLYADFSHD T. thermophilus         PAQGVGFvNE LIARMTHSPV QDYTTVNHTL DSNPATFPLN
ATLYADFSHD M. thermophila          PTQGVGFvNE LLARLAgvPV RDgTSTNRTL DGDPrTFPLG
rPLYADFSHD
```

FIG. 1I

| | | |
|---|---|---|
| Consensus ATLYADFSHD | PAQGVGF-NE LIARLTHSPV | QDHTSTNHTL DSNPATFPLN |
| Consensus phytase ATLYADFSHD | PAQGVGFANE LIARLTRSPV | QDHTSTNHTL DSNPATFPLN |

351                                          400

| | | |
|---|---|---|
| A. terreus 9A-1 FAARAYVEMM | SNLVSIFWAL GLYNGTAPLS | qTSVESVSQT DGYAAAWTVP |
| A. terreus cbs FAARAYIEMM | SNLVSIFWAL GLYNGTkPLS | qTTVEDITrT DGYAAAWTVP |
| A. niger var. awamori FASRlYVEMM | NGIISILFAL GLYNGTkPLS | TTTVENITQT DGFSSAWTVP |
| A. niger T213 FASRlYVEMM | NGIISILFAL GLYNGTkPLS | TTTVENITQT DGFSSAWTVP |
| A. niger NRRL3135 FASRlYVEMM | NGIISILFAL GLYNGTkPLS | TTTVENITQT DGFSSAWTVP |
| A. fumigatus 13073 FGARAYFEtM | NSMVSIFFAL GLYNGTEPLS | rTSVESaKEl DGYSASWVVP |
| A. fumigatus 32722 FGARAYFEtM | NSMVSIFFAL GLYNGTGPLS | rTSVESaKEl DGYSASWVVP |
| A. fumigatus 58128 FGARAYFEtM | NSMVSIFFAL GLYNGTEPLS | rTSVESaKEl DGYSASWVVP |
| A. fumigatus 26906 FGARAYFEtM | NSMVSIFFAL GLYNGTEPLS | rTSVESaKEl DGYSASWVVP |
| A. fumigatus 32239 FGARAYFEtM | NGMIPIFFAM GLYNGTEPLS | qTSeESTKES NGYSASWAVP |

FIG. 1J

| | | |
|---|---|---|
| A. nidulans | NSMISIFFAM GLYNGTQPLS mDSVESIQEm DGYAASWTVP FGARAYFELM | |
| T. thermophilus | NTMTSIFaAL GLYNGTAkLS TTEIKSIEET DGYSAAWTVP FGGRAYIEMM | |
| M. thermophila | NDMMGVLgAL GaYDGVPPLD KTArrDpEEl GGYAASWAVP FAARiYVEKM | |
| Consensus | NSMISIFFAL GLYNGTAPLS TTSVESIEET DGYAASWTVP FGARAYVEMM | |
| Consensus phytase | NSMISIFFAL GLYNGTAPLS TTSVESIEET DGYSASWTVP FGARAYVEMM | |

```
                         401                                           450
A. terreus 9A-1          QC........ .....RAEKE PLVRVLVNDR VMPLHGCPTD KLGRCKrDAF
A. terreus cbs           QC........ .....RAEKQ PLVRVLVNDR VMPLHGCAVD NLGRCKrDDF
A. niger var. awamori    QC........ .....QAEQE PLVRVLVNDR VVPLHGCPID aLGRCTrDSF
A. niger T213            QC........ .....QAEQE PLVRVLVNDR VVPLHGCPID aLGRCTrDSF
A. niger NRRL3135        QC........ g....QAEQE PLVRVLVNDR VVPLHGCPVD aLGRCTrDSF
A. fumigatus 13073       QC........ .....KSEKE PLVRALINDR VVPLHGCDVD KLGRCKLNDF
A. fumigatus 32722       QC........ .....KSEKE PLVRALINDR VVPLHGCDVD KLGRCKLNDF
```

FIG. 1K

```
A. fumigatus 58128    QC........ .....KSEKE SLVRALINDR VVPLHGCDVD
KLGRCKLNDF
A. fumigatus 26906    QC........ .....KSEKE PLVRALINDR VVPLHGCDVD
KLGRCKLNDF
A. fumigatus 32239    QC........ .....KSEKE PLVRALINDR VVPLHGCAVD
KLGRCKLKDF
A. nidulans           QC........ .....E.KKE PLVRVLVNDR VVPLHGCAVD
KFGRCTLDDW
T. thermophilus       QC........ .....DDSDE PVVRVLVNDR VVPLHGCEVD
SLGRCKrDDF
M. thermophila        RCsggggggg ggegrQEKDE eMVRVLVNDR VMTLkGCGAD
ErGMCTLErF Consensus             QC-------- -----QAEKE PLVRVLVNDR VVPLHGCAVD
KLGRCKLDDF
Consensus phytase     QC........ .....QAEKE PLVRVLVNDR VVPLHGCAVD
KLGRCKRDDF
```

FIG. 1L

```
                              451              471
A. terreus 9A-1        VAGLSFAQAG GNWADCF~~~ ~
A. terreus cbs         VEGLSFARAG GNWAECF~~~ ~
A. niger var. awamori  VrGLSFARSG GDWAECsA~~ ~
A. niger T213          VrGLSFARSG GDWAECFA~~ ~
A. niger NRRL3135      VrGLSFARSG GDWAECFA~~ ~
A. fumigatus 13073     VKGLSWARSG GNWGECFS~~ ~
A. fumigatus 32722     VKGLSWARSG GNWGECFS~~ ~
A. fumigatus 58128     VKGLSWARSG GNWGECFS~~ ~
A. fumigatus 26906     VKGLSWARSG GNWGECFS~~ ~
A. fumigatus 32239     VKGLSWARSG GNSEQSFS~~ ~
A. nidulans            VEGLNFARSG GNWkTCFT1~ ~
T. thermophilus        VrGLSFARqG GNWEGCYAas e
M. thermophila         IESMAFARGN GKWD1CFA~~ ~

Consensus              VEGLSFARSG GNWAECFA-- -
Consensus phytase      VEGLSFARSG GNWAECFA.. .
```

FIG. 1M

```
                 CP-1
         EcoRI   M  G  V  F  V  V  L  L  S  I  A  T  L  F  G  S  T
       TATATGAATTCATGGGCGTGTTCGTCGTGCTACTGTCCATTGCCACCTTGTTCGGTTCCA
     1 ----------+---------+---------+---------+---------+---------+
    60
       ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G
       CATCCGGTACCGCCTTGGGTCCTCGTGGTAATTCTCACTCTTGTGACACTGTTGACGGTG
    61 ----------+---------+---------+---------+---------+---------+
   120
       GTAGGCCATGGCGGAACCCAGGAGCACCATTAAGAGTGAGAACACTGTGACAACTGCCAC
                                                              CP-2
                   CP-3
           Y  Q  C  F  P  E  I  S  H  L  W  G  Q  Y  S  P  Y  F  S  L
       GTTACCAATGTTTCCCAGAAATTTCTCACTTGTGGGGTCAATACTCTCCATACTTCTCTT
   121 ----------+---------+---------+---------+---------+---------+
   180
       CAATGGTTACAAAGGGTCTTTAAAGAGTGAACACCCCAGTTATGAGAGGTATGAAGAGAA

E  D  E  S  A  I  S  P  D  V  P  D  D  C  R  V  T  F  V  Q
       TGGAAGACGAATCTGCTATTTCTCCAGACGTTCCAGACGACTGTAGAGTTACTTTCGTTC
   181 ----------+---------+---------+---------+---------+---------+
   240
       ACCTTCTGCTTAGACGATAAAGAGGTCTGCAAGGTCTGCTGACATCTCAATGAAAGCAAG
                                 CP-4
                                       CP-5
           V  L  S  R  H  G  A  R  Y  P  T  S  S  K  S  K  A  Y  S  A
       AAGTTTTGTCTAGACACGGTGCTAGATACCCAACTTCTTCTAAGTCTAAGGCTTACTCTG
```

FIG. 2A

241 ---------+---------+---------+---------+---------+---------+
300
TTCAAAACAGATCTGTGCCACGATCTATGGGTTGAAGAAGATTCAGATTCCGAATGAGAC

```
          L    I    E    A    I    Q    K    N    A    T    A    F    K    G    K    Y    A    F    L    K
```
CTTTGATTGAAGCTATTCAAAAGAACGCTACTGCTTTCAAGGGTAAGTACGCTTTCTTGA
301 ---------+---------+---------+---------+---------+---------+
360
GAAACTAACTTCGATAAGTTTTCTTGCGATGACGAAAGTTCCCATTCATGCGAAAGAACT

CP-6

CP-7

```
          T    Y    N    Y    T    L    G    A    D    D    L    T    P    F    G    E    N    Q    M    V
```
AGACTTACAACTACACTTTGGGTGCTGACGACTTGACTCCATTCGGTGAAAACCAAATGG
361 ---------+---------+---------+---------+---------+---------+
420
TCTGAATGTTGATGTGAAACCCACGACTGCTGAACTGAGGTAAGCCACTTTTGGTTTACC

```
          N    S    G    I    K    F    Y    R    R    Y    K    A    L    A    R    K    I    V    P    F
```
TTAACTCTGGTATTAAGTTCTACAGAAGATACAAGGCTTTGGCTAGAAAGATTGTTCCAT
421 ---------+---------+---------+---------+---------+---------+
480
AATTGAGACCATAATTCAAGATGTCTTCTATGTTCCGAAACCGATCTTTCTAACAAGGTA

```
              I  R  A  S  G  S  D  R  V  I  A  S  A  E  K  F  I  E  G  F
         TCATTAGAGCTTCTGGTTCTGACAGAGTTATTGCTTCTGCTGAAAAGTTCATTGAAGGTT
     481 ---------+---------+---------+---------+---------+---------+
     540
         AGTAATCTCGAAGACCAAGACTGTCTCAATAACGAAGACGACTTTTCAAGTAACTTCCAA

Q  S  A  K  L  A  D  P  G  S  Q  P  H  Q  A  S  P  V  I  D
         TCCAATCTGCTAAGTTGGCTGACCCAGGTTCTCAACCACACCAAGCTTCTCCAGTTATTG
     541 ---------+---------+---------+---------+---------+---------+
     600
         AGGTTAGACGATTCAACCGACTGGGTCCAAGAGTTGGTGTGGTTCGAAGAGGTCAATAAC
                                                        CP-10

CP-11
              V  I  I  P  E  G  S  G  Y  N  N  T  L  D  H  G  T  C  T  A
         ACGTTATTATTCCAGAAGGaTCcGGTTACAACAACACTTTGGACCACGGTACTTGTACTG
     601 ---------+---------+---------+---------+---------+---------+
     660
         TGCAATAATAAGGTCTTCCtAGgCCAATGTTGTTGTGAAACCTGGTGCCATGAACATGAC
```

FIG. 2C

```
              F  E  D  S  E  L  G  D  D  V  E  A  N  F  T  A  L  F  A  P
        CTTTCGAAGACTCTGAATTGGGTGACGACGTTGAAGCTAACTTCACTGCTTTGTTCGCTC
    661 ---------+---------+---------+---------+---------+---------+
    720
        GAAAGCTTCTGAGACTTAACCCACTGCTGCAACTTCGATTGAAGTGACGAAACAAGCGAG
                                                                CP-12

A  I  R  A  R  L  E  A  D  L  P  G  V  T  L  T  D  E  D  V
        CAGCTATTAGAGCTAGATTGGAAGCTGACTTGCCAGGTGTTACTTTGACTGACGAAGACG
    721 ---------+---------+---------+---------+---------+---------+
    780
        GTCGATAATCTCGATCTAACCTTCGACTGAACGGTCCACAATGAAACTGACTGCTTCTGC

CP-13
              V  Y  L  M  D  M  C  P  F  E  T  V  A  R  T  S  D  A  T  E
        TTGTTTACTTGATGGACATGTGTCCATTCGAAACTGTTGCTAGAACTTCTGACGCTACTG
    781 ---------+---------+---------+---------+---------+---------+
    840
        AACAAATGAACTACCTGTACACAGGTAAGCTTTGACAACGATCTTGAAGACTGCGATGAC

L  S  P  F  C  A  L  F  T  H  D  E  W  R  Q  Y  D  Y  L  Q
        AATTGTCTCCATTCTGTGCTTTGTTCACTCACGACGAATGGAGACAATACGACTACTTGC
    841 ---------+---------+---------+---------+---------+---------+
    900
        TTAACAGAGGTAAGACACGAAACAAGTGAGTGCTGCTTACCTCTGTTATGCTGATGAACG
                CP-14
                   CP-15
              S  L  G  K  Y  Y  G  Y  G  A  G  N  P  L  G  P  A  Q  G  V
```

FIG. 2D

```
               AATCTTTGGGTAAGTACTACGGTTACGGTGCTGGTAACCCATTGGGTCCAGCTCAAGGTG
       901  ---------+---------+---------+---------+---------+---------+
       960
               TTAGAAACCCATTCATGATGCCAATGCCACGACCATTGGGTAACCCAGGTCGAGTTCCAC

G  F  A  N  E  L  I  A  R  L  T  R  S  P  V  Q  D  H  T  S
               TTGGTTTCGCTAACGAATTGATTGCTAGATTGACTAGATCTCCAGTTCAAGACCACACTT
       961  ---------+---------+---------+---------+---------+---------+
      1020
               AACCAAAGCGATTGCTTAACTAACGATCTAACTGATCTAGAGGTCAAGTTCTGGTGTGAA
                              CP-16
                                CP-17
                 T  N  H  T  L  D  S  N  P  A  T  F  P  L  N  A  T  L  Y  A
               CTACTAACCACACTTTGGACTCTAACCCAGCTACTTTCCCATTGAACGCTACTTTGTACG
      1021  ---------+---------+---------+---------+---------+---------+
      1080
               GATGATTGGTGTGAAACCTGAGATTGGGTCGATGAAAGGGTAACTTGCGATGAAACATGC

D  F  S  H  D  N  S  M  I  S  I  F  F  A  L  G  L  Y  N  G
               CTGACTTCTCTCACGACAACTCTATGATTTCTATTTTCTTCGCTTTGGGTTTGTACAACG
      1081  ---------+---------+---------+---------+---------+---------+
      1140
               GACTGAAGAGAGTGCTGTTGAGATACTAAAGATAAAAGAAGCGAAACCCAAACATGTTGC
                                                  CP-18
                                                    CP-19
                 T  A  P  L  S  T  T  S  V  E  S  I  E  E  T  D  G  Y  S  A
               GTACTGCTCCATTGTCTACTACTTCTGTTGAATCTATTGAAGAAACTGACGGTTACTCTG
```

FIG. 2E

1141 ---------+---------+---------+---------+---------+---------+
1200
        CATGACGAGGTAACAGATGATGAAGACAACTTAGATAACTTCTTTGACTGCCAATGAGAC

S   W   T   V   P   F   G   A   R   A   Y   V   E   M   M   Q   C   Q   A   E
        CTTCTTGGACTGTTCCATTCGGTGCTAGAGCTTACGTTGAAATGATGCAATGTCAAGCTG
1201 ---------+---------+---------+---------+---------+---------+
1260
        GAAGAACCTGACAAGGTAAGCCACGATCTCGAATGCAACTTTACTACGTTACAGTTCGAC
                                                 CP-20

CP-21
         K   E   P   L   V   R   V   L   V   N   D   R   V   V   P   L   H   G   C   A
        AAAAGGAACCATTGGTTAGAGTTTTGGTTAACGACAGAGTTGTTCCATTGCACGGTTGTG
1261 ---------+---------+---------+---------+---------+---------+
1320
        TTTTCCTTGGTAACCAATCTCAAAACCAATTGCTGTCTCAACAAGGTAACGTGCCAACAC

FIG. 2F

```
            V  D  K  L  G  R  C  K  R  D  D  F  V  E  G  L  S  F  A  R
         CTGTTGACAAGTTGGGTAGATGTAAGAGAGACGACTTCGTTGAAGGTTTGTCTTTCGCTA
   1321  ---------+---------+---------+---------+---------+---------+
1380
         GACAACTGTTCAACCCATCTACATTCTCTCTGCTGAAGCAACTTCCAAACAGAAAGCGAT
                                                        CP-22
            S  G  G  N  W  A  E  C  F  A  *  Eco RI
         GATCTGGTGGTAACTGGGCTGAATGTTTCGCTTAAGAATTCATATA
   1381  ---------+---------+---------+---------+------ 1426
         CTAGACCACCATTGACCCGACTTACAAAGCGAATTCTTAAGTATAT
```

FIG. 2G

CONSENSUS PHYTASES

This is a divisional of U.S. application Ser. No. 09/121,425, filed Jul. 23, 1998, now U.S. Pat. No. 6,153,418.

BACKGROUND OF THE INVENTION

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A phytase was first described in rice bran in 1907 [Suzuki et al., Bull. Coll. Agr. Tokio Imp. Univ. 7, 495 (1907)] and phytases from Aspergillus species in 1911 [Dox and Golden, J. Biol. Chem. 10, 183–186 (1911)]. Phytases have also been found in wheat bran, plant seeds, animal intestines and in microorganisms [Howsen and Davis, Enzyme Microb. Technol. 5, 377–382 (1983), Lambrechts et al., Biotech. Lett. 14, 61–66 (1992), Shieh and Ware, Appl. Microbiol. 16, 1348–1351 (1968)].

The cloning and expression of the phytase from *Aspergillus niger* (ficuum) has been described by Van Hartingsveldt et al., in Gene, 127, 87–94 (1993) and in European Patent Application, Publication No. (EP) 420 358 and from *Aspergillus niger* var. *awamori* by Piddington et al., in Gene 133, 55–62 (1993).

Cloning, expression and purification of phytases with improved properties have been disclosed in EP 684 313. However, since there is a still ongoing need for further improved phytases, especially with respect to the thermostability, it is an object of the present invention to provide the following process which is, however, not only applicable to phytases.

SUMMARY OF THE INVENTION

The invention herein is a process for the preparation of a consensus protein, especially a phytase. The invention is also directed to a consensus phytase and to a DNA sequence encoding the consensus phytase. As is well known, a consensus protein is a new protein whose sequence is created from sequence information obtained from at least three other proteins having a similar biological activity. The object in preparing a consensus protein is to obtain a single protein which combines the advantageous properties of the original proteins.

The process is characterized by the following steps:

a) at least three preferably four amino acid sequences of a defined protein family are aligned by any standard alignment program known in the art;

b) amino acids at the same position according to such alignment are compared regarding their evolutionary similarity by any standard program known in the art, whereas the degree of similarity provided by such a program which defines the least similarity of the amino acids that is used for the determination of an amino acid of corresponding positions is set to a less stringent number and the parameters are set in such a way that it is possible for the program to determine from only 2 identical amino acids at a corresponding position an amino acid for the consensus protein; however, if among the compared amino acid sequences are sequences that show a much higher degree of similarity to each other than to the residual sequences, the sequences are represented by their consensus sequence determined as defined in the same way as in the present process for the consensus sequence of the consensus protein or a vote weight of 1 divided by the number of such sequences is assigned to every of those sequences.

c) in case no common amino acid at a defined position can be identified by the program, any of the amino acids of all sequences used for the comparison, preferably the most frequent amino acid of all such sequences is selected or an amino acid is selected on the basis of the consideration given in Example 2.

d) once the consensus sequence has been defined, such sequence is back-translated into a DNA sequence, preferably using a codon frequency table of the organism in which expression should take place;

e) the DNA sequence is synthesized by methods known in the art and used either integrated into a suitable expression vector or by itself to transform an appropriate host cell;

f) the transformed host cell is grown under suitable culture conditions and the consensus protein is isolated from the host cell or its culture medium by methods known in the art.

In a preferred embodiment of this process step b) can also be defined as follows: b) amino acids at the same position according to such an alignment are compared regarding their evolutionary similarity by any standard program known inthe art, whereas the degree of similarity provided by such program is set at the lowest possible value and the amino acid which is the most similar for at least half of the sequences used for the comparison is selected for the corresponding position in the amino acid sequence of the consensus protein.

Thus the claimed invention is a process for obtaining a consensus protein from a group of amino acid sequences of a defined protein family, which comprises:

a) aligning a group consisting of three to one hundred, but preferably three or four amino acid sequences from a defined protein family;

b) comparing the evolutionary similarity of amino acids which occupy a position in the aligned sequences to select a consensus amino acid for said position using a system which is so organized that if two amino acids which occupy said position are identical, then the identical amino acid is selected as the consensus amino acid for said position, unless three or more other amino acids at said position have a higher degree of structural similarity to each other than to the identical amino acid, in which case the amino acid which has the highest degree of evolutionary similarity to the other amino acids is selected as the consensus amino acid for said position, with the proviso that if a set of amino acid sequences exists within the group of step a) such that the amino acid sequences within the set have more evolutionary similarity to each other than to any of the amino acid sequences of the group which are not part of the set, then the amino acids which occupy said position in members of the set will have a vote weight of one divided by the number of amino acid sequences in the set where the amino acids which occupy said position in amino acid sequences which are not in the set will have a vote weight of one, and repeating the procedure for each position in the aligned group of amino acid sequences;

c) if no consensus amino acid for said position is obtained by the method of step b), then any amino acid at said position is selected as the consensus sequence, preferably the most frequent amino acid;

d) combining the consensus amino acids obtained in steps b) and c) obtain a consensus amino acid sequence;

e) translating the consensus amino acid sequence into a DNA sequence, preferably using a codon frequency table specific to whichever host organism has been selected for expressing the DNA sequence;

f) obtaining the DNA sequence and using said DNA sequence to express a protein which is the consensus protein of the defined protein family.

The present invention is also directed to new phytases, preferably phytases having the amino acid sequence depicted in FIG. 2 and variants and muteins thereof. In addition, the invention includes polynucleotides which encode such new phytases.

BRIEF DESCRIPTION OF THE DRAWINGS

FIG. 1: Calculation of the consensus phytase sequence from the alignment of nearly all known fungal phytase amino acid sequences. The letters represent the amino acid residues in the one-letter code. The following sequences were used for the alignment: phyA from *Aspergillus terreus* 9A-1 (Mitchell et al., 1997; from amino acid (aa) 27), phyA from *Aspergillus terreus* cbs116.46 (van Loon et al., 1997; from aa 27), phyA from *Aspergillus niger* var. *awamori* (Piddington et al., 1993; from aa 27), phyA from *Aspergillus niger* T213; from aa 27), phyA from *Aspergillus niger* strain NRRL3135 (van Hartingsveldt et al., 1993; from aa 27), phyA from *Aspergillus fumigatus* ATCC 13073 (Pasamontes et al., 1997b; from aa 25), phyA from *Aspergillus fumigatus* ATCC 32722 (van Loon et al., 1997; from aa 27), phyA from *Aspergillus fumigatus* ATCC 58128 (van Loon et al., 1997; from aa 27), phyA from *Aspergillus fumigatus* ATCC 26906 (van Loon et al., 1997; from aa 27) phyA from *Aspergillus fumigatus* ATCC 32239 (van Loon et al., 1997; from 30), phyA from *Aspergillus nidulans* (Pasamontes et al., 1997a; from aa 25 phyA from *Talaromyces thermophilus* (Pasamontes et al., 1997a; from aa 24), and phyA from *Myceliophthora thermophila* (Mitchell et al., 1997; from aa 19). The alignment was calculated using the program PILEUP. The location of the gaps was refined by hand. Capitalized amino acid residues in the alignment at a given position belong to the amino acid coalition that establish the consensus residue. In bold, beneath the calculated consensus sequence, the amino acid sequence of the finally constructed fungal consensus phytase (Fcp) is shown. The gaps in the calculated consensus sequence were filled by hand according to principals stated in Example 2.

FIG. 2: DNA sequence of the fungal consensus phytase gene (fcp) and of the primers synthesized for gene construction. The calculated amino acid sequence (FIG. 1) was converted into a DNA sequence using the program BACKTRANSLATE (Devereux et al., 1984) and the codon frequency table of highly expressed yeast genes (GCG program package, 9.0). The signal peptide of the phytase from *A. terreus* cbs was fused to the N-terminus. The bold bases represent the sequences of the oligonucleotides used to generate the gene. The names of the respective oligonucleotides are noted above or below the sequence. The underlined bases represent the start and stop codon of the gene. The bases written in italics show the two introduced Eco RI sites.

DETAILED DESCRIPTION OF THE INVENTION

Figure 3:
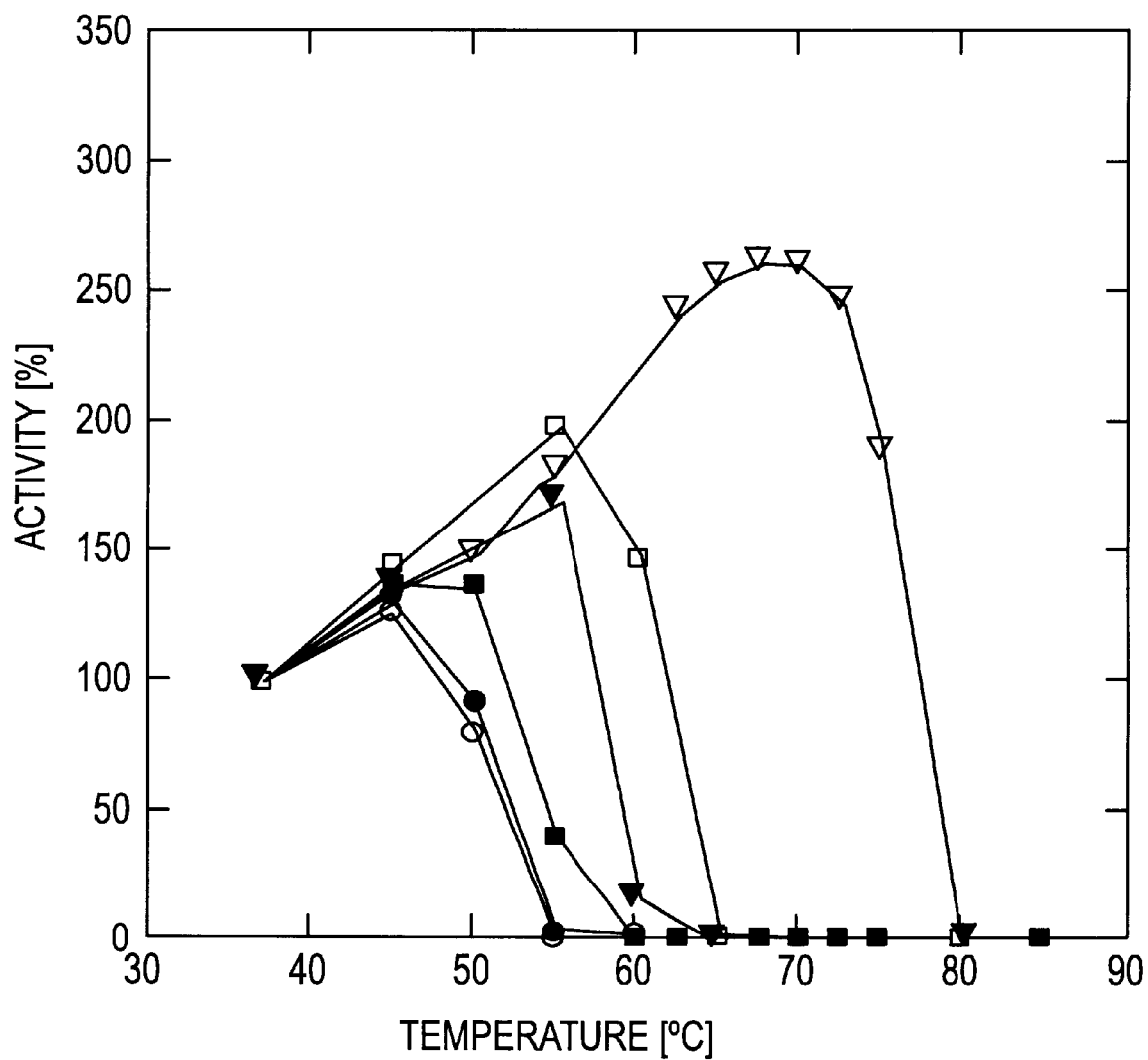
FIG. 3: Temperature optimum of fungal consensus phytase and other phytases used to calculate the consensus sequence. For the determination of the temperature optimum, the phytase standard assay was performed at a series of temperatures between 37 and 85° C. The phytases used were purified according to Example 5. ▽, fungal consensus phytase; ▲, *A. fumigatus* 13073 phytase; □, *A. niger* NRRL3135 phytase; ○, *A. nidulans* phytase; ■, *A. terreus* 9A-1 phytase; ●, *A. terreus* cbs phytase.

A preferred embodiment of this whole process can be seen in a process in which a sequence is choosen from a number of highly homologous sequences and only those amino acid residues are replaced which clearly differ from a consensus, sequence of this protein family calculated under moderately stringent conditions, while at all positions of the alignment where the method is not able to determine an amino acid under moderately stringent conditions the amino acids of the preferred sequence are taken.

It is furthermore an object of the present invention to provide such a process, wherein the program used for the comparison of amino acids at a defined position regarding their evolutionary similarity is the program "PRETTY". It is more specifically an object of the present invention to provide such a process, wherein the defined protein family is the family of phytases, especially wherein the phytases are of fungal origin.

It is furthermore an object of the present invention to provide such processes, wherein the host cell is of eukaryotic, especially fungal, preferably Aspergillus or yeast, preferably Saccharomyces or Hansenula origin. It is also an object of the present invention to provide a consensus protein obtainable by such a process. A preferred consensus protein obtained by the present process is of the defined protein family of phytases. The especially preferred consensus phytase is created based on phytase sequences from:

*Aspergillus terreus* 9A-1, aa 27 (Mitchell et al., 1997);

*Aspergillus terreus* cbs116.46, aa 27 (van Loon et al., 1997);

*Aspergillus niger* var. *awamori*, aa 27 (Piddington et al., 1993);

*Aspergillus niger* T213, aa 27;

*Aspergillus niger* strain NRRL3135, aa 27 (van Hartingsveldt et al., 1993);

*Aspergillus fumigatus* ATCC 13073, aa 26 (Pasamontes et al., 1997);

*Aspergillus fumigatus* ATCC 32722, aa 26 (van Loon et al., 1997);

*Aspergillus fumigatus* ATCC 58128, aa 26 (van Loon et al., 1997);

*Aspergillus fumigatus* ATCC 26906, aa 26 (van Loon et al., 1997);

*Aspergillus fumigatus* ATCC 32239, aa 30 (van Loon et al., 1997);

*Aspergillus nidulans*, aa 25 (Pasamontes et al., 1997a);

*Talaromyces thermophilus* ATCC 20186, aa 24 (Pasamontes et al., 1997a); and

*Myceliophthora thermophila*, aa 19 (Mitchell et al., 1997). Therefore the preferred group of amino acid sequences used in the process of this invention is the amino acid sequences encoding the phytases of the above fungi.

The preferred phytase of the invention is a consensus protein whose sequence is created based on the sequences of the twelve phytases shown in Table 3, below, but which is not highly homologous to any of the twelve phytases in that the consensus phytase is not more than about 80% identical to any of the twelve phytases. The present invention is particularly directed to a consensus phytase which has the amino acid sequence shown in FIG. 2 or a variant or mutein thereof. The consensus phytase of FIG. 2 is not highly homologous to any of the twelve phytases which were used to create its sequence, as can be seen from the sequence comparison results shown in Table 3. Another consensus phytase of this invention has the sequence shown in FIG. 1 as consensus phytase (bottom line in boldface type) or a variant or mutein thereof.

A "variant" of the consensus phytase with amino acid sequence shown in FIG. 1 or preferably FIG. 2 is the consensus phytase of Figure or preferably FIG. 2 in which at one or more positions amino acids have been deleted, added or replaced by one or more other amino acids with the proviso that the resulting sequence provides for a phytase whose basic properties like enzymatic activity (type of and specific activity), thermostability, activity in a certain pH-range (pH-stability) have not significantly been changed. "Significantly" means in this context that a skilled person would say that the properties of the variant may still be different but would not be unobvious over the ones of the consensus phytase with the amino acid sequence of FIG. 1 or FIG. 2 itself.

A mutein refers in the context of the present invention to replacements of the amino acid in the amino acid sequence of the consensus protein shown in FIG. 1 o preferably FIG. 2 which lead to consensus proteins with further improved properties, e.g., activity. Such muteins can be defined and prepared on the basis of the teachings given in European Patent Application number 97810175.6, e.g., Q50L, Q50T, Q50G, Q50L-Y51N, or Q50T-Y51N. "Q50L" means in this context that at position 50 of the amino acid sequence the amino acid Q has been replaced by amino acid L. Therefore specific muteins of this invention include a mutein which has the amino acid sequence of FIG. 2 except that Q at position 50 has been replaced by L, T, or G, and two muteins which have the amino acid sequence of FIG. 1 except that Q at position 50 has been replaced by T or L and Y at position 51 has been replaced by N.

Polynucleotides which encode the consensus phytase of this invention, i.e., a phytase with the amino acid sequence of FIG. 1 or preferably FIG. 2 or variants and muteins thereof, especially the specific muteins listed above, are also part of this invention. Such polynucleotides may be obtained by known methods, for example by backtranslation of the mutein's amino acid sequence and PCR synthesis of the corresponding polynucleotide as described below.

In addition, a food, feed, premix or pharmaceutical composition comprising a consensus protein as defined above is also an object of the present invention. Food, feed, and premix compositions, preferably for domestic livestock, are well known to a skilled person, as are pharmaceutical compositions. Such pharmaceutical compositions are likely to be veterinary compositions formulated for oral ingestion, such as pills and the like.

In this context "at least three preferably four amino acid sequences of such defined protein family" means that three, four, five, six to 12, 20, 50, 100 or even more sequences can be used for the alignment and the comparison to create the amino acid sequence of the consensus protein. Amino acid sequences may be obtained from known sources such as publications or databases, or may be deduced by translation of DNA sequences which are publicly available, or may be determined by known techniques for sequencing an isolated protein or obtaining and sequencing a gene encoding a protein and translating the DNA sequence. "Sequences of a defined protein family" means that such sequences fold into a three dimensional structure, wherein the α-helixes, the β-sheets and-turns are at the same position so that such structures are, as called by the skilled person, superimposable. Furthermore these sequences characterize proteins which show the same type of biological activity, e.g., a defined enzyme class such as the phytases. As known in the art, the three dimensional structure of one of such sequences is sufficient to allow the modelling of the structure of the other sequences of such a family. An example, how this can be effected, is given in the Reference Example of the present case.

Aligning amino acid sequences is a well known process whereby two or more amino acids are lined up in such a way to maximize the intern amino acid sequences which they have in common.

"Evolutionary similarity" in the context of the present invention refers to a schema which classifies amino acids regarding their structural similarity which allows that one amino acid can be replaced by another amino acid with a minimal influence on the overall structure, as this is done e.g. by programs, like "PRETTY", known in the art. The phrase "the degree of similarity provided by such a program . . . is set to less stringent number" means in the context of the present invention that values for the parameters which determine the degree of similarity in the program used in the practice of the present invention are chosen in a way to allow the program to define a common amino acid for a maximum of positions of the whole amino acid sequence, e.g. in case of the program PRETTY a value of 2 or 3 for the THRESHOLD and a value of 2 for the PLURALITY can be choosen.

A consensus amino acid is an amino acid chosen to occupy a given position in the consensus protein obtained by this method. A system which is organized to select consensus amino acids as described above may be a computer program, or a combination of one or more computer programs with "by hand" analysis and calculation. A set of amino acid sequences existing within the group of amino acid sequences from which the consensus sequence is prepared means a set of such sequences which are more similar to each other than to other members of the group, based on the evolutionary similarity analysis performed above. An example of such a group is a species where a set with in the group would be members of a particular strain. Furthermore, "a vote weight of one divided by the number of such sequence means in the context of the present invention that the sequences which define a group of sequences with a higher degree of similarity as the other sequences used for the determination of the consensus sequence only contribute to such determination with a factor which is equal to one divided by a number of all sequences of this group. Thus an amino acid occupying a particular position in the aligned sequences will, if it is a member of a set, not have a comparison value of equal weight with the other amino acids (e.g. one) but will have a lower weight depending on the size of the set which it is in, as the weight is one divided by the number of amino acid sequences in the set.

When a consensus amino acid is obtained for each position of the aligned amino acid sequences, then these consensus amino acids are "lined up" to obtain the, amino acid sequence of the consensus protein.

As mentioned before should the program not allow selection of the most similar amino acid, the most frequent amino acid is selected, should the latter be impossible the skilled person will select an amino acid from all the sequences used for the comparison which is known in the art for its property to improve the thermostability in proteins as discussed, e.g., by:

Janecek, S. (1993), *Process Biochem.* 28, 435–445 or

Fersht, A. R. & Serrano, L. (1993), *Curr. Opin. Struct. Biol.* 3, 75–83.

Alber, T. (1989), *Annu. Rev. Biochem.* 58, 765–798 or

Matthews, B. W. (1987), *Biochemistry* 26, 6885–6888.

Matthews, B. W. (1991), *Curr. Opin. Struct. Biol.* 1, 17–21.

The stability of an enzyme is a critical factor for many industrial applications. Therefore, a lot of attempts, more or less successful, have been made to improve the stability, preferably the thermostability, of enzymes be rational (van den Burg et al., 1998) or irrational approaches (Akanuma et al., 1998). The forces influencing the thermostability of a protein are the same those that are responsible for the proper folding of a peptide strand (hydrophobic interactions, van der Waals interactions, H-bonds, salt bridges, conformational strain (Matthews, 1993). Furthermore, as shown by Matthews et al. (1987), the free energy of the unfolded state has also an influence on the stability of a protein. Enhancing of protein stability means to increase the number and strength of favorable interactions and to decrease the number and strength of unfavorable interactions. It has been possible to introduce disulfide linkages (Sauer et al., 1986) to replace glycine with alanine residues or to increase the proline content in order to reduce the free energy of the unfolded state (Margarit et al., 1992; Matthews, 1987a). Other groups concentrated on the importance of additional H-bonds or salt bridges for the stability of a protein (Blaber et al., 1993) or tried to fill cavities in the protein interior to increase the buried hydrophobic surface area and the van der Waals interactions (Karpusas et al., 1989). Furthermore, the stabilization of secondary structure elements, especially α-helices, for example, by improved helix capping, was also investigated (Munoz & Serrano, 1995).

However, there is no fast and promising strategy to identify amino acid replacements which will increase the stability, preferably the thermal stability of a protein. Commonly, the 3D structure of a protein is required to find locations in the molecule where an amino acid replacement possibly will stabilize the protein's folded state. Alternative ways to circumvent this problem are either to search for a homologous protein in a thermo- or hyperthermophile organism or to detect stability-increasing amino acid replacements by a random mutagenesis approach. This latter possibility succeeds in only $10^3$ to $10^4$ mutations and is restricted to enzymes for which fast screening procedure is available (Arase et al., 1993; Risse et al., 1992). For all these approaches, success was variable and unpredictable and, if successful, the thermostability enhancements nearly always were rather small.

Here we present an alternative way to improve the thermostability of a protein. Imanaka et al. (1986) were among the first to use the comparisons of homologous proteins to enhance the stability of a protein. They used a comparison of proteases from thermophilic with homologous ones of mesophilic organisms to enhance the stability of a mesophilic protease. Serrano et al. (1993) used the comparison of the amino acid sequences of two homologous mesophilic RNases to construct a more thermostable Rnase. They mutated individually all of the residues that differ between the two and combined the mutations that increase the stability in a multiple mutant. Pantoliano et al. (1989) and, in particular, Steipe et al. (1994) suggested that the most frequent amino acid at every position of an alignment of homologous proteins contribute to the largest amount to the stability of a protein. Steipe et al. (1994) proved this for a variable domain of an immunoglobulin, whereas Pantoliano et al. (1989) looked for positions in the primary sequence of subtilisin in which the sequence of the enzyme chosen to be improved for higher stability was singularly divergent. Their approach resulted in the replacement M50F which increased the $T_m$ of subtilisin by 1.8° C.

Steipe et al. (1994) proved on a variable domain of immunoglobulin that it is possible to predict a stabilizing mutation with better than 60% success rate just by using a statistical method which determines the most frequent amino acid residue at a certain position of this domain. It was also suggested that this method would provide useful results not only for stabilization of variable domains of antibodies but also for domains of other proteins. However, it was never mentioned that this method could extended to the entire protein. Furthermore, nothing is said about the program which was used to calculate the frequency of amino acid residues a distinct position or whether scoring matrices were used as in the present case.

It is therefore an object of the present invention to provide a process for the preparation of a consensus protein comprising a process to calculate an amino acid residue for nearly all positions of a so-called consensus protein and to synthesize a complete gene from this sequence that could be expressed in a pro- or eukaryotic expression system.

DNA sequences from which amino acid sequences may be derived for making consensus proteins of the present invention, can be constructed starting from genomic or cDNA sequences coding for proteins, e.g. phytases known in the state of the art [for sequence information see references mentioned above, e.g. EP 684 313 or sequence data bases, for example like Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA) or disclosed in the figures by methods of in vitro mutagenesis [see e.g. Sambrook et al., Molecular Cloning, Cold Spring Harbor Laboratory Press, New York]. A widely used strategy for such "site directed mutagenesis", as originally outlined by Hurchinson and Edgell [J. Virol. 8, 181 (1971)], involves the annealing of a synthetic oligonucleotide carrying the desired nucleotide substitution to a target region of a single-stranded DNA sequence wherein the mutation should be introduced [for review see Smith, Annu. Rev. Genet. 19, 423 (1985) and for improved methods see references 2–6 in Stanssen et al. Nucl. Acid Res., 17, 4441–4454 (1989)].

Another possibility of mutating a given DNA sequence which is also preferred for the practice of the present invention is the mutagenesis using the polymerase chain reaction (PCR). DNA as starting material can be isolated by methods known in the art and described e.g. in Sambrook et al. (Molecular Cloning) from the respective strains. For strain information see, e.g., EP 684 313 or any depository authority indicated below. *Aspergillus niger* [ATCC 9142], *Myceliophthora thermophila* [ATCC 48102], *Talaromyces thermophilus* [ATCC 20186] and *Aspergillus fumigatus* [ATCC 34625] have been redeposited, according to the conditions of the Budapest Treaty at the American Type Culture Cell Collection under the following accession numbers: ATCC 74337, ATCC 74340, ATCC 74338 and ATCC 74339, respectively. Amino acid sequences may be obtained by know methods from these DNA sequences for use in the process of this invention to obtain a consensus protein. It is however, understood that DNA encoding a consensus protein in accordance with the present invention can also be prepared in a synthetic manner as described, e.g. in EP 747 483 or the examples by methods known in the art.

Once complete DNA sequences of the present invention have been obtained (for example by synthesis based on backtranslation of a consensus protein obtained in accordance with the invention) they can be integrated into vectors by methods known in the art and described e.g. in Sambrook et al. (s.a.) to overexpress the encoded polypeptide in appropriate host systems. However, a skilled person knows that also the DNA sequences themselves can be used to transform the suitable host systems of the invention to get overexpression of the encoded polypeptide. Appropriate host systems are for example fungi, like Aspergilli, e.g. *Aspergillus niger* [ATCC 9142] or *Aspergillus ficuum* [NRRL 3135] or like Trichoderma, e.g. *Trichoderma reesei* or yeasts, like Saccharomyces, e.g. *Saccharomyces cerevisiae* or Pichia, like *Pichia pastoris*, or *Hansenula polymorpha*, e.g. *H. polymorpha* (DSM5215) plants, as described, e.g. by Pen et al., Bio/Technology 11, 811–814 (1994). skilled person knows that such microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSM) or any other depository authority as listed in the Journal "Industrial Property" [(1991) 11 pages 29–40]. Bacteria which can be used are e.g. *E. coli*, Bacilli as, e.g. *Bacillus subtilis* or Streptomyces, e.g. *Streptomyces lividans* (see e.g. Anné and Mallaert in FEMS Microbiol. Letters 114, 121 (1993). *E. coli*, which could be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Vectors which can be used for expression in fungi are known in the art and described e.g. in EP 420 358, or by Cullen et al. [Bio/Technology 5, 369–376 (1987)] or Ward in Molecular Industrial Mycology, Systems and Applications for Filamentous Fungi, Marcel Dekker, New York (1991), Upshall et al. [Bio/Technology 5, 1301–1304 (1987)] Gwynne et al. [Bio/Technology 5, 71–79 (1987)], Punt et al. [J. Biotechnol. 17, 19–34 (1991)] and for yeast by Sreekrishna et al. [J. Basic Microbiol. 28, 265–278 (1988), Biochemistry 28, 4117–4125 (1989)], Hitzemann et al. [Nature 293, 717–722 (1981)] or in EP 183 070, EP 183 071, EP 248 227, EP 263 311. Suitable vectors which can be used for expression in *E. coli* are mentioned, e.g. by Sambrook et al. [s.a.] or by Fiers et al. in Procd. 8th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, e.g. in EP 405 370, Procd. Natl. Acad. Sci. USA 81, 439 (1984) by Yansura and Henner, Meth. Enzymol. 185, 199–228 (1990) or EP 207 459. Vectors which can be used for the expression in *H. polymorpha* are known in the art and described, e.g. in Gellissen et al., Biotechnology 9, 291–295 (1991).

Either such vectors already carry regulatory elements, e.g., promotors, or the DNA sequences of the present invention can be engineered to contain such elements. Suitable promotor elements which can be used are known in the art and are, e.g. for *Trichoderma reesei* the cbh1-[Haarki et al., Biotechnology 7, 596–600 (1989)] or the pki1-promoter [Schindler et al., Gene 130, 271–275 (1993)], for *Aspergillus oryzae* the amy-promotor [Christensen et al., Abstr. 19th Lunteren Lectures on Molecular Genetics F23 (1987), Christensen et al., Biotechnology 6, 1419–1422 (1988), Tada et al., Mol. Gen. Genet. 229, 301 (1991)], for *Aspergillus niger* the glaA-[Cullen et al., Bio/Technology 5, 369–376 (1987), Gwynne et al., Bio/Technology 5, 713–719 (1987), Ward in Molecular Industrial Mycology, Systems and Applications for Filamentous Fungi, Marcel Dekker, New York, 83–106 (1991)], alcA-[Gwynne et al., Bio/Technology 5, 718–719 (1987)], suc1-[Boddy et al., Curr. Genet. 24, 60–66 (1993)], aphA-[MacRae et al., Gene 71, 339–348 (1988), MacRae et al., Gene 132, 193–198 (1993)], tpiA-[McKnight et al., Cell 46, 143–147 (1986), Upshall et al., Bio/Technology 5, 1301–1304 (1987)], gpdA-[Punt et al., Gene 69, 49–57 (1988), Punt et al., J. Biotechnol. 17, 19–37 (1991)] and the pkiA-promotor [de Graaff et al., Curr. Genet. 22, 21–27 (1992)]. Suitable promotor elements which could be used for expression in yeast are known in the art and are, e.g. the pho5-promotor [Vogel et al., Mol. Cell. Biol., 2050–2057 (1989); Rudolf and Hinnen, Proc. Natl. Acad. Sci. 84, 1340–1344 (1987)] or the gap-promotor for expression in *Saccharomyces cerevisiae* and for *Pichia pastoris*, e.g. the aox1-promotor [Koutz et al., Yeast 5, 167–177 (1989); Sreekrishna et al., J. Basic Microbiol. 28, 265–278 (1988)], or the FMD promoter [Hollenberg et al., EPA No. 0299108] or MOX-promotor [Ledeboer et al., Nucleic Acids Res. 13, 3063–3082 (1985)] for *H. polymorpha*.

Accordingly vectors comprising DNA sequences of the present invention, preferably for the expression of said DNA sequences in bacteria or a fungal or a yeast host and such transformed bacteria or fungal or yeast hosts are also an object of the present invention.

It is also an object of the present invention to provide a system which allows for high expression of proteins, preferably phytases like the consensus phytase of the present invention in Hansenula characterized therein that the codons of the encoding DNA sequence of such a protein have been selected on the basis of a codon frequency table of the organism used for expression, e.g. yeast as in the present case (see e.g. in Example 3) and optionally the codons for the signal sequence have been selected in a manner as described for the specific case in Example 3. That means that a codon frequency table is prepared on the basis of the codons used in the DNA sequences which encode the amino acid sequences of the defined protein family. Then the codons for the design of the DNA sequence of the signal sequence are selected from a codon frequency table of the host cell used for expression whereby always codons of comparable frequency in both tables are used.

Once such DNA sequences have been expressed in an appropriate host cell in a suitable medium the encoded protein can be isolated either from the medium in the case the protein is secreted into the medium or from the host organism in case such protein is present intracellularly by methods known in the art of protein purification or described in case of a phytase, e.g. in EP 420 358. Accordingly a process for the preparation of a consensus protein (i.e. a polypeptide) of the present invention characterized in that transformed bacteria or a host cell as described above is cultured under suitable culture conditions and the consensus protein is recovered therefrom and a consensus protein produced by such a process or a consensus protein encoded by a DNA sequence of the present invention are also an object of the present invention.

Once obtained, the consensus proteins (i.e. polypeptides), preferably phytases, of the present invention can be characterized regarding their properties which make them useful in agriculture. Any assay known in the art may be used such as those described, e.g., by Simons et al. [Br. J. Nutr. 64, 525–540 (1990)], Schöner et al. [J. Anim. Physiol. a. Anim. Nutr. 66, 248–255 (1991)], Vogt [Arch. Geflügelk. 56, 93–98 (1992)], Jongbloed et al. [J. Anim. Sci., 70, 1159–1168 (1992)], Perney et al. [Poultry Sci. 72, 2106–2114 (1993)], Farrell et al., [J. Anim. Physiol. a. Anim. Nutr. 69, 278–283 (1993), Broz et al., [Br. Poultry Sci. 35, 273–280 (1994)] and Düngelhoef et al. [Animal Feed Sci. Technol. 49, 1–10 (1994)].

In general the consensus phytases of the present invention can be used without being limited to a specific field of application, e.g., in case of phytases for the conversion of inositol polyphosphates, like phytate to inositol and inorganic phosphate.

Furthermore the consensus phytases of the present invention can be used in a process for the preparation of a pharmaceutical composition or compound food or feeds wherein the components of such a composition are mixed with one or more consensus phytases of the present invention. Accordingly compound food or feeds or pharmaceutical compositions comprising one or more consensus phytases of the present invention are also an object of the present invention. A skilled person is familiar with their process of preparation. Such pharmaceutical compositions or compound foods or feeds can further comprise additives or components generally used for such purpose and known in the state of the art.

It is furthermore an object of the present invention to provide a process for the reduction of levels of phytate in animal manure characterized in that an animal is fed such a feed composition in an amount effective in converting phytate contained in the feedstuff to inositol and inorganic phosphate.

The Examples which follow further elucidate the invention but are not intended to limit it in any way.

EXAMPLES

Reference Example

Homology Modeling of *A. fumigatus* and *A. terreus* cbs116.46 Phytase

The amino acid sequences of *A. fumigatus* and *A. terreus* cbs116.46 phytase were compared with the sequence of *A. niger* NRRL 3135 phytase (see FIG. 1) for which the three-dimensional structure had been determined by X-ray crystallography.

A multiple amino acid sequence alignment of *A. niger* NRRL 3135 phytase, *A fumigatus* phytase and *A. terreus* cbs116.46 phytase was calculated with the program "PILEUP" (Prog. Menu for the Wisconsin Package, version 8, September 1994, Genetics Computer.Group, 575 Science Drive, Madison Wis., USA 53711). The three-dimensional models of *A. fumigatus* phytase and *A. terreus* cbs116.46 phytase were built by using the structure of *A. niger* NRRL 3135 phytase as template and exchanging the amino acids of *A. niger* NRRL 3135 phytase according to the sequence alignment to amino acids of *A. fumigatus* and *A. terreus* cbs116.46 phytases, respectively. Model construction and energy optimization were performed by using the program Moloc (Gerber and Müller, 1995). C-alpha positions were kept fixed except for new insertions/deletions and in loop regions distant from the active site.

Only small differences of the modelled structures to the original crystal structure could be observed in external loops. Furthermore the different substrate molecules that mainly occur on the degradation pathway of phytic acid (myo-inositol-hexakisphosphate) by Pseudomonas sp. *bacterium* phytase and, as far as determined, by *A. niger* NRRL 3135 phytase (Cosgrove, 1980) were constructed and forged into the active site cavity of each phytase structure. Each of these substrates was oriented in a hypothetical binding mode proposed for histidine acid phosphatases (Van Etten, 1982). The scissile phosphate group was oriented towards the catalytically essential His 59 to form the covalent phosphoenzyme intermediate. The oxygen of the substrate phosphoester bond which will be protonated by Asp 339 after cleavage was orientated towards the proton donor. Conformational relaxation of the remaining structural part of the substrates as well as the surrounding active site residues was performed by energy optimization with the program Moloc.

Based on the structure models the residues pointing into the active site cavity were identified. More than half (60%) of these positions were identical between these three phytases, whereas only few positions were not conserved (see FIG. 1). This observation could be extended to four additional phytase sequences (*A. nidulans, A. terreus* 9A1, *Talaromyces thermophilus, Myceliophthora thermophila*).

Example 1

Alignment of the Amino Acid Sequence of the Fungal Phytases

The alignment was calculated using the program PILEUP from the Sequence Analysis Package Release 9.0 (Devereux et al., 1984) with the standard parameter (gap creation penalty 12, gap extension penalty 4). The location of the gaps was refined using a text editor. Amino acid sequences encoded by the following genes (see FIG. 1) without the signal sequence were used for the performance of the alignment starting with the amino acid (aa) mentioned below:

phyA gene from *Aspergillus terreus* 9A-1, aa 27 (Mitchell et al., 1997)

phyA gene from *Aspergillus terreus* cbs116.46, aa 27 (van Loon et al., 1997)

phyA gene from *Aspergillus niger* var. *awamori*, aa 27 (Piddington et al., 1993)

phyA gene from *Aspergillus niger* T213, aa 27 phyA gene from *Aspergillus niger* strain NRRL3135, aa 27 (van Hartingsveldt et al., 1993)

phyA gene from *Aspergillus fumigatus* ATCC 13073, aa 26 (Pasamontes et al., 1997)

phyA gene from *Aspergillus fumigatus* ATCC 32722, aa 26 (van Loon et al., 1997)

phyA gene from *Aspergillus fumigatus* ATCC 58128, aa 26 (van Loon et al., 1997)

phyA gene from *Aspergillus fumigatus* ATCC 26906, aa 26 (van Loon et al., 1997)

phyA gene from *Aspergillus fumigatus* ATCC 32239, aa 30 (van Loon et al., 1997)

phyA gene from *Aspergillus nidulans*, aa 25 (Pasamontes et al., 1997a)

phyA gene from *Talaromyces thermophilus* ATCC 20186, aa 24 (Pasamontes et al., 1997a)

phyA gene from *Myceliophthora thermophila*, aa 19 (Mitchell et al., 1997)

Table 2 shows the homology of the phytase sequences mentioned above.

PRETTY from the Sequence Analysis Package Release 9.0 (Devereux et al., 1984). PRETTY prints sequences with their columns aligned and can display a consensus sequence for the alignment. A vote weight that pays regard to the similarity between the amino acid sequences of the phytases aligned were assigned to all sequences. The vote weight was set such as the combined impact of all phytases from one sequence subgroup (same species of origin but different strains), e.g. the amino acid sequences of all phytases from *A. fumigatus*, on the election was set one, that means that each sequence contributes with a value of 1 divided by the number of strain sequences (see Table 1). By this means, it was possible to prevent that very similar amino acid sequences, e.g. of the phytases from different *A. fumigatus* strains, dominate the calculated consensus sequence.

TABLE 1

| | |
|---|---|
| *Aspergillus terreus* 9A-1 phytase: | 0.50 |
| *Aspergillus terreus* cbs116.46 phytase: | 0.50 |
| *Aspergillus niger* var. *awamori* phytase: | 0.3333 |
| *Aspergillus niger* T213 phytase: | 0.3333 |
| *Aspergillus niger* NRRL3135 phytase: | 0.3333 |
| *Aspergillus fumigatus* ATCC 13073 phytase: | 0.20 |
| *Aspergillus fumigatus* ATCC 32722 phytase: | 0.20 |
| *Aspergillus fumigatus* ATCC 58128 phytase: | 0.20 |
| *Aspergillus fumigatus* ATCC 26906 phytase: | 0.20 |
| *Aspergillus fumigatus* ATCC 32239 phytase: | 0.20 |
| *Aspergillus nidulans* phytase: | 1.00 |
| *Talaromyces thermophilus* ATCC 20186 phytase: | 1.00 |
| *Myceliophthora thermophila* phytase: | 1.00 |

Table 1: Vote weights of the amino acid sequences of the fungal phytases used. The table shows the vote weights used to calculate the consensus sequence of the fungal phytases.

TABLE 2

| | % identity | | | | | | |
|---|---|---|---|---|---|---|---|
| | A. terreus 9A-1 | A. terreus cbs 116.46 | A. niger NRRL 3135 | A. fumigatus 13073 | A. nidulans | T. thermophilus | M. thermophila |
| A. terreus 9A-1 | | 89.1 | 62.0 | 60.6 | 59.3 | 58.3 | 48.6 |
| A. terreus cbs | 90.7 | | 63.6 | 62.0 | 61.2 | 59.7 | 49.1 |
| A. niger NRRL 3135 | 67.3 | 68.9 | | 66.8 | 64.2 | 62.5 | 49.4 |
| A. fumigatus 13073 | 66.1 | 67.2 | 71.1 | | 68.0 | 62.6 | 53.0 |
| A. nidulans | 65.0 | 66.7 | 69.0 | 73.3 | | 60.5 | 52.5 |
| T. thermophilus | 63.8 | 64.5 | 68.9 | 68.1 | 67.4 | | 49.8 |
| M. thermophila | 53.7 | 54.6 | 57.6 | 61.0 | 59.9 | 57.8 | |
| | | | | % similarity | | | |

Table 2: Homology of the fungal phytases. The amino acid sequences of the phytases used in the alignment were compared by the program GAP (GCG program package, 9; Devereux et al., 1984) using the standard parameters. The comparison was restricted to the part of the sequence that was also used for the alignment (see legend to FIG. 1) lacking the signal peptide which was rather divergent. The numbers above and beneath the diagonal represent the amino acid identities and similarities, respectively.

Example 2
Calculation of the Amino Acid Sequence of Fungal Consensus Phytases

Using the refined alignment of Example 1 as input, the consensus sequence was calculated by the program The program PRETTY was started with the following parameters: The plurality defining the number of votes below which there is no consensus was set on 2.0. The threshold, which determines the scoring matrix value below which an amino acid residue may not vote for a coalition of residues, was set on 2. PRETTY used the PrettyPep.Cmp consensus scoring matrix for peptides.

Ten positions of the alignment (position 46, 66, 82, 138, 162, 236, 276, 279, 280, 308; FIG. 1), for which the program was not able to determine a consensus residue, were filled by hand according to the following rules: if a most frequent residue existed, this residue was chosen (138, 236, 280); if a prevalent group of chemically similar or equivalent residues occurred, the most frequent or, if not available, one residues of this group was selected (46, 66,;82, 162, 276, 308). If there was either a prevalent residue nor a prevalent group, one of the occurring residues was chosen according to common assumption on their influence on the protein stability (279). Eight other positions (132, 170, 204, 211, 275, 317, 384, 447; FIG. 1) were not filled with the amino acid residue selected by the program but normally with amino acids that occur with the same frequency as the residues that were chosen by the program. In most cases, the slight underrating of the three *A. niger* sequences (sum of the vote weights: 0.99) was eliminated by this corrections.

Table 3 shows the homology of the calculated fungal consensus phytase amino acid sequence to the phytase sequences used for the calculation.

TABLE 3

| Phytase | Identity [%] | Similarity [%] |
|---|---|---|
| A. niger T213 | 76.6 | 79.6 |
| A. niger var. awamori | 76.6 | 79.6 |
| A. niger NRRL3135 | 76.6 | 79.4 |
| A. nidulans | 77.4 | 81.5 |
| A. terreus 9A-1 | 70.7 | 74.8 |
| A. terreus cbs116.46 | 72.1 | 75.9 |
| A. fumigatus 13073 | 80.0 | 83.9 |
| A. fumigatus 32239 | 78.2 | 82.3 |
| T. thermophilus | 72.7 | 76.8 |
| M. thermophila | 58.3 | 64.5 |

Table 3: Homology of the amino acid sequence of fungal consensus phytase to the phytases used for its calculation. The amino acid sequences of all phytases were compared with the fungal consensus phytase sequence using the program GAP (GCG program package, 9.0). Again, the comparison was restricted to that part of the sequence that was used in the alignment.

Example 3

Conversion of the Fungal Consensus Phytase Amino acid Sequence to a DNA Sequence The first 26 amino acid residues of *A. terreus* cbs116.46 phytase were used as signal peptide and, therefore, fused to the N-terminus of all consensus phytases. For this stretch, we used a special method to calculate the corresponding DNA sequence. Purvis et al. (1987) proposed that the incorporation of rare codons in a gene has an influence on the folding efficiency of the protein. Therefore, at least the distribution of rare codons in the signal sequence of *A. terreus* cbs116.46, which was used for the fungal consensus phytase and which is very important for secretion of the protein, but converted into the *S. cerevisiae* codon usage, was transferred into the new signal sequence generated for expression in *S. cerevisiae*. For the remaining parts of the protein, we used the codon frequency table of highly expressed *S. cerevisiae* genes, obtained from the GCG program package, to translate the calculated amino acid sequence into a DNA sequence. The resulting sequence of the fcp gene are shown in FIG. 2.

Example 4

Construction and Cloning of the Fungal Consensus Phytase Genes

The calculated DNA sequence of fungal consensus phytase was divided into oligonucleotides of 85 bp, alternately using the sequence of the sense and the anti-sense strand. Every oligonucleotide overlaps 20 bp with its previous and its following oligonucleotide of the opposite strand. The location of all primers, purchased by Microsynth, Balgach (Switzerland) and obtained in a PAGE-purified form, is indicated in FIG. 2. In three PCR reactions, the synthesized oligonucleotides were composed to the entire gene. For the PCR, the High Fidelity Kit from Boehringer Mannheim (Boehringer Mannheim, Mannheim, Germany) and the thermo cycler The Protokol™ from AMS Biotechnology (Europe) Ltd. (Lugano, Switzerland) were used.

Oligonucleotide CP-1 to CP-10 (Mix 1, FIG. 2) were mixed to a concentration of 0.2 pMol/µl per each oligonucleotide. A second oligonucleotide mixture (Mix 2) was prepared with CP-9 to CP-22 (0.2 pMol/µl per each oligonucleotide). Additionally, four short primers were used in the PCR reactions:

| | |
|---|---|
| CP-a: | Eco RI<br>5'-TAT ATG AAT TCA TGG GCG TGT TCG TC-3' |
| CP-b: | 5'-TGA AAA GTT CAT TGA AGG TTT C-3' |
| CP-c: | 5'-TCT TCG AAA GCA GTA CAA GTA C-3' |
| CP-e: | Eco RI<br>5'-TAT ATG AAT TCT TAA GCG AAA C-3' |

PCR reaction a: 10 µl Mix 1 (2.0 pmol of each oligonucleotide)
  2 µnucleotides (10 mM each nucleotide)
  2 µl primer CP-a (10 pmol/µl)
  2 µl primer CP-c (10 pmol/µl)
  10,0 µl PCR buffer
  0.75 µl polymerase mixture
  73.25 µl H$_2$O PCR reaction b: 10 µl Mix 2 (2.0 pmol of each oligonucleotide)
  2 µl nucleotides (10 mM each nucleotide)
  2 µl primer CP-b (10 pmol/µl)
  2 µl primer CP-e (10 pmol/µl)
  10,0 µl PCR buffer
  0.75 µl polymerase mixture (2.6 U)
  73.25 µl H$_2$O Reaction conditions for PCR reaction a and b:
  step 1 2 min—45° C.
  step 2 30 sec—72° C.
  step 3 30 sec—94° C.
  step 4 30 sec—52° C.
  step 5 1 min—72° C.

Step 3 to 5 were repeated 40-times.

The PCR products (670 and 905 bp) were purified by an agarose gel electrophoresis (Q.9% agarose) and a following gel extraction (QIAEX II Gel Extraction Kit, Qiagen, Hilden, Germany). The purified DNA fragments were used for the PCR reaction c.

PCR reaction c: 6 µl PCR product of reaction a (≈50 ng)
  6 µl PCR product of reaction b (≈50 ng)
  2 µl primer CP-a (10 pmol/µl)
  2 µl primer CP-e (10 pmol/µl)
  10,0 µl PCR buffer
  0.75 µl polymerase mixture (2.6 U)
  73.25 µl H$_2$O Reaction conditions for PCR reaction c:
   step 1 2 min—94° C.
   step 2 30 sec—94° C.
   step 3 30 sec—55° C.
   step 4 1 min—72° C.
Step 2 to 4 were repeated 31-times.

The resulting PCR product (1.4 kb) was purified as mentioned above, digested with Eco RI, and ligated in an Eco RI-digested and dephosphorylated pBsk(−)-vector (Stratagene, La Jolla, Calif., USA). 1 μl of the ligation mixture was used to transform E. coli XL-1 competent cells (Stratagene, La Jolla, Calif., USA). All standard procedures were carried out as described by Sambrook et al. (1987). The constructed fungal consensus phytase gene (fcp) was verified by sequencing (plasmid pBsk⁻-fcp).

Example 5

Expression of the Fungal Consensus Phytase Gene fcp and its Variants in *Saccharomyces cerevisiae* and Their Purification from Culture Supernatant A fungal consensus phytase gene was isolated from the plasmid pBsk⁻fcp ligated into the Eco RI sites of the expression cassette of the *Saccharomyces cerevisiae* expression vector pYES2 (Invitrogen, San Diego, Calif., USA) or subcloned between the shortened GAPFL (glyceraldhyde-3-phosphate dehydrogenase) promoter and the pho5 terminator as described by Janes et al. (1990). The correct orientation of the gene was checked by PCR. Transformation of S. cerevisiae strains. e.g. INVSc1 (Invitrogen, San Diego, Calif., USA) was done according to Hinnen et al. (1978). Single colonies harboring the phytase gene under the control of the GAPFL promoter were picked and cultivated in 5 ml selection medium (SD-uracil, Sherman et al., 1986) at 30° C. under vigorous shaking (250 rpm) for one day. The preculture was then added to 500 ml YPD medium (Sherman et al., 1986) and grown under the same conditions. Induction of the gal1 promoter was done according to manufacturer's instruction. After four days of incubation cell broth was centrifuged (7000 rpm, GS3 rotor, 15 min, 5° C.) to remove the cells and the supernatant was concentrated by way of ultrafiltration in Amicon 8400 cells (PM30 membranes) and ultrafree-15 centrifugal filter devices (Biomax-30K, Millipore, Bedford, Mass., USA). The concentrate (10 ml) was desalted on a 40 ml Sephadex G25 Superfine column (Pharmacia Biotech, Freiburg, Germany), with 10 mM sodium acetate, pH 5.0, serving as elution buffer. The desalted sample was brought to 2 M $(NH_4)_2SO_4$ and directly loaded onto a 1 ml Butyl Sepharose 4 Fast Flow hydrophobic interaction chromatography column (Pharmacia Biotech, Feiburg, Germany) which was eluted with a linear gradient from 2 M to 0 M $(NH_4)_2SO_4$ in 10 mM sodium acetate, pH 5.0. Phytase was eluted in the break-through, concentrated and loaded on a 120 ml Sephacryl S-300 gel permeation chromatography column (Pharmacia Biotech, Freiburg, Germany). Fungal consensus phytase and fungal consensus phytase 7 eluted as a homogeneous symmetrical peak and was shown by SDS-PAGE to be approx. 95% pure.

Example 6

Expression of the Fungal Consensus Phytase Genes fcp and its Variants in *Hansenula polymorpha*

The phytase expression vectors, used to transform *H. polymorpha*, was constructed by inserting the Eco RI fragment of pBsk⁻fcp encoding the consensus phytase or a variant into the multiple cloning site of the *H. polymorpha* expression vector pFPMT121, which is based on an ura3 selection marker and the FMD promoter. The 5' end of the fcp gene is fused to the FMD promoter, the 3' end to the MOX terminator (Gellissen et al., 1996; EP 0299 108 B). The resulting expression vector are designated pFPMTfcp and pBsk⁻fcp7.

The constructed plasmids were propagated in *E. coli*. Plasmid DNA was purified using standard state of the art procedures. The expression plasmids were transformed into the *H. polymorpha* strain RP11 deficient in orotidine-5'-phosphate decarboxylase (ura3) using the procedure for preparation of competent cells and for transformation of yeast as described in Gelissen et al. (1996). Each transformation mixture was plated on YNB (0.14% w/v Difco YNB and 0.5% ammonium sulfate) containing 2% glucose and 1.8% agar and incubated at 37° C. After 4 to 5 days individual transformant colonies were picked and grown in the liquid medium described above for 2 days at 37° C. Subsequently, an aliquot of this culture was used to inoculate fresh vials with YNB-medium containing 2% glucose. After seven further passages in selective medium, the expression vector integrates into the yeast genome in multimeric form. Subsequently, mitotically stable transformants were obtained by two additional cultivation steps in 3 ml non-selective liquid medium (YPD, 2% glucose, 10 g yeast extract, and 20 g peptone). In order to obtain genetically homogeneous recombinant strains an aliquot from the last stabilization culture was plated on a selective plate. Single colonies were isolated for analysis of phytase expression in YNB containing 2% glycerol instead of glucose to derepress the fmd promoter. Purification of the fungal consensus phytases was done as described in Example 5.

Example 7

Expression of the Fungal Consensus Genes fcp and its Variants in *Aspergillus niger*

Plasmid pBsk⁻fcp or the corresponding plasmid of a variant of the fcp gene were used as template for the introduction of a Bsp HI-site upstream of the start codon of the genes and an Eco RV-site downstream of the stop codon. The Expand™ High Fidelity PCR Kit (Boehringer Mannheim, Mannheim, Germany) was used with the following primers:

```
Primer Asp-1:
        Bsp HI
 5'-TAT ATC ATG AGC GTG TTC GTC GTG CTA CTG TTC-3'

Primer Asp-2 for cloning of fcp and fcp7:
 3'-ACC CGA CTT ACA AAG CGA ATT CTA TAG ATA TAT-5'
                                  Eco RV
```

The reaction was performed as described by the supplier. The PCR-amplified fcp gene had a new Bsp HI site at the start codon, introduced by primer Asp-1, which resulted in a replacement of the second amino acid residue glycine by serine. Subsequently, the DNA-fragment was digested with Bsp HI and Eco RV and ligated into the Nco I site downstream of the glucoamylase promoter of *Aspergillus niger* (glaA) and the Eco RV site upstream of the *Aspergillus nidulans* tryptophan C terminator (trpC) (Mullaney et al., 1985). After this cloning step, the genes were sequenced to detect possible failures introduced by PCR. The resulting expression plasmids which basically corresponds to the pGLAC vector as described in Example 9 of EP 684 313, contained the orotidine-5'-phosphate decarboxylase gene (pyr4) of Neurospora crassa as a selection marker. Transformation of Aspergillus tiger and expression of the consensus phytase genes was done as described in EP 684 313. The fungal consensus phytases were purified as described in Example 5.

Example 8

Construction of Muteins of Fungal Consensus Phytase

To construct muteins for expression in A. niger, S. cerevisiae, or H. polymorpha, the corresponding expression plasmid containing the fungal consensus phytase gene was used as template for site-directed mutagenesis. Mutations were introduced using the "quick exchange™ site-directed mutagenesis kit" from Stratagene (La Jolla, Calif., USA) following the manufacturer's protocol and using the corresponding primers. All mutations made and the corresponding primers are summarized in Table 4. Clones harboring the desired mutation were identified by DNA sequence analysis as known in the art. The mutated phytase were verified by sequencing of the complete gene.

activity was defined as the amount of enzyme that releases 1 μmol phosphate per minute at 37° C. The protein concentration was determined using the enzyme extinction coefficient at 280 nm calculated according to Pace et al. (1995): fungal consensus phytase, 1.101; fungal consensus phytase 7, 1.068. In case of pH-optimum curves, purified enzymes were diluted in 10 mM sodium acetate, pH 5.0. Incubations were started by mixing aliquots of the diluted protein with an equal volume of 1% phytic acid (≈10 mM) in a series of different buffers: 0.4 M glycine/HCl, pH 2.5; 0.4 M acetate/NaOH, pH 3.0, 3.5, 4.0, 4.5, 5.0, 5.5; 0.4 M imidazole/HCl, pH 6.0, 6.5; 0.4 M Tris/HCl pH 7.0, 7.5, 8.0, 8.5, 9.0. Control experiments showed that pH was only slightly affected by the mixing step. Incubations were performed for 15 min at 37° C. as described above.

For determination of the substrate specificities of the phytases, phytic acid in the assay mixture was replaced by 5 mM concentrations of the respective phosphate compounds. The activity tests were performed as described above.

For determination of the temperature optimum, enzyme (100 μl) and substrate solution (100 μl) were pre-incubated for 5 min at the given temperature. The reaction was started by addition of the substrate solution to the enzyme. After 15

TABLE 4

| mutation | Primer set |
|---|---|
| t1,1 | Ssp BI |
| Q50L | 5'-CAC TTG TGG GGT TTG TAC AGT CCA TAC TTC TC-3'<br>5'-GAG AAG TAT GGA CTG TAC AAA CCC CAC AAG TG-3' |
| | Kpn I |
| Q50T | 5'-CAC TTG TGG <u>GGT ACC</u>TAC TCT CCA TAC TTC TC-3'<br>5'-GA GAA GTA TGG AGA GTA GGT ACC CCA CAA GTG-3' |
| Q50G | 5'-CAC TTG TGG GGT GGT TAC TCT CCA TAC TTC TC-3'<br>5'-GA GAA GTA TGG AGA GTA ACC ACC CCA CAA GTG-3' |
| | Kpn I |
| Q50T-Y51N | 5'-CAC TTG TGG <u>GGT ACC</u> AAC TCT CCA TAC TTC TC-3'<br>5'-GA GAA GTA TGG AGA GTT GGT ACC CCA CAA GTG-3' |
| | Bsa I |
| Q50L-Y51N | 5'-CAC TTG TGG <u>GGT CTC</u> AAC TCT CCA TAC TTC TC-3'<br>5'-GA GAA GTA TGG AGA GTT GAG ACC CCA CAA GTG-3' |

Table 4: Primers used for the introduction of single mutations into fungal consensus phytase. For the introduction of each mutation, two primers containing the desired mutation were required (see Example 8). The changed triplets are highlighted in bold letters.

Example 9

Determination of the Phytase Activity and of the Temperature Optimum of the Consensus Phytase and its Variants Phytase activity was determined basically as described by Mitchell et al. (1997). The activity was measured in a assay mixture containing 0.5% phytic acid (≈5 mM), 200 mM sodium acetate, pH 5.0. After 15 min incubation at 37° C., the reaction was stopped by addition of an equal volume of 15% trichloroacetic acid. The liberated phosphate was quantified by mixing 100 μl of the assay mixture with 900 μl H₂O and 1 ml of 0.6 M H₂SO₄, 2% ascorbic acid and 0.5% ammonium molybdate. Standard solutions of potassium phosphate were used as reference. One unit of enzyme min incubation, the reaction was stopped with trichloroacetic acid and the amount of phosphate released was determined.

Figure 4A:
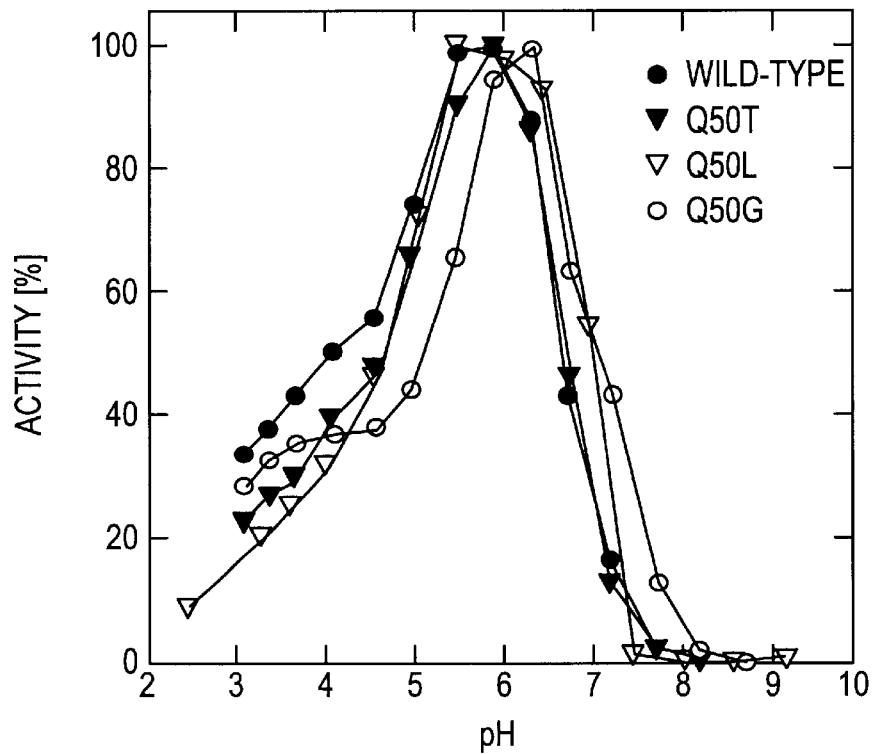
FIG. 4: The pH-dependent activity profile of fungal consensus phytase and of the mutant Q50L, Q50T, and Q50G. The phytase activity was determined using the standard assay in appropriate buffers (see Example 9) at different pH-values. Plot: a) shows a comparison of fungal consensus phytase (●) to the mutants Q50L (▽), Q50T (▲), and Q50G (○) in percent activity. Plot b) shows a comparison of fungal consensus phytase (○) to mutant Q50L (●) and Q50T (▽) using the specific activity of the purified enzymes expressed in *H. polymorpha*.
Figure 4B:
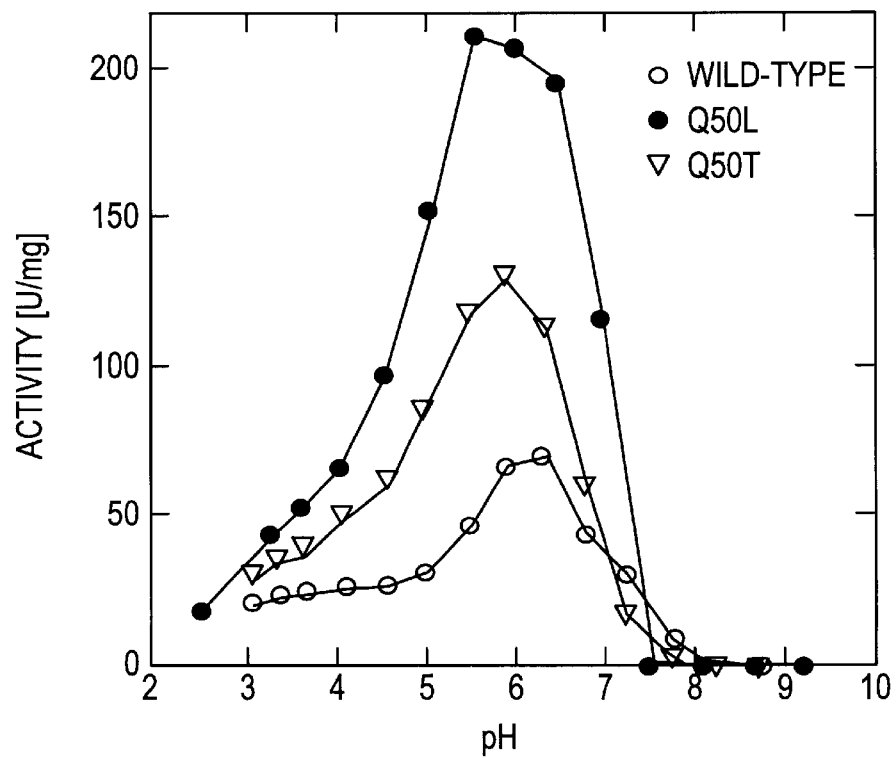
Figure 5A:
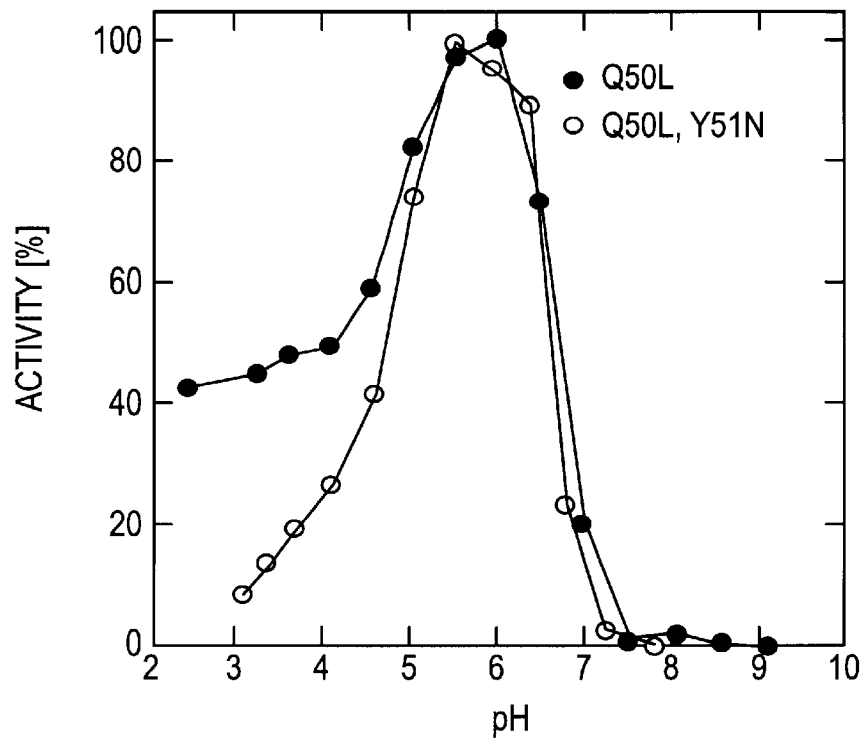
FIG. 5: The pH-dependent activity profile of the mutants Q50L, Y51N and Q50T, Y51N in comparison to the mutants Q50T and Q50L of fungal consensus phytase. The phytase activity was determined using the standard assay in appropriate buffers (see Example 9) at different pH-values. Graph a) shows the influence of the mutation Y51N (●) on mutant Q50L (○). Graph b) shows the influence of the same mutation (●) on mutant Q50T (○).
Figure 5B:
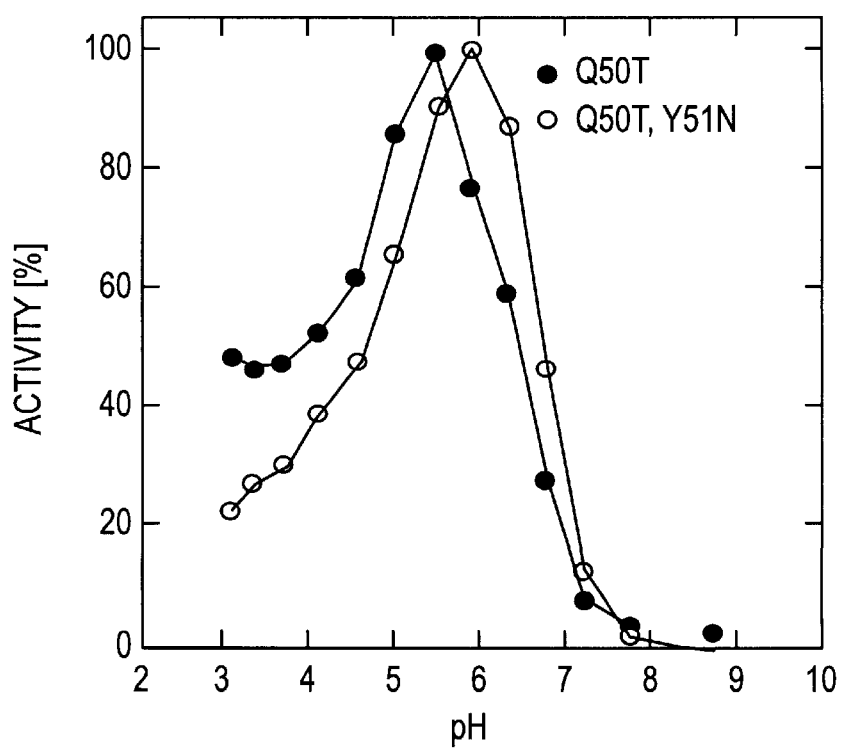
Figure 6:
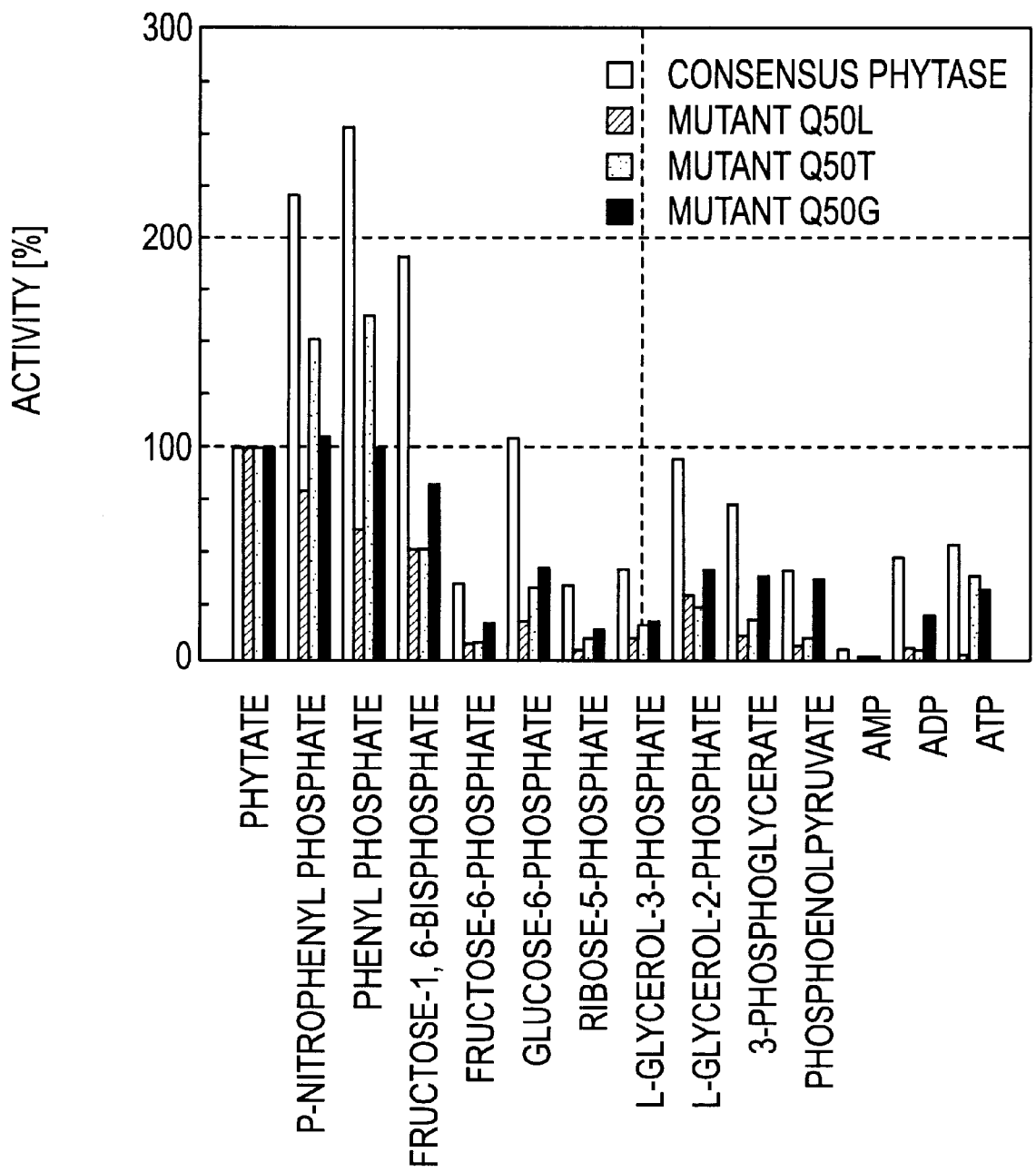
FIG. 6: Substrate specificity of fungal consensus phytase and its mutants Q50L, Q50T, and Q50G. The bars represent the relative activity in comparison to the activity with phytic acid (100%) with a variety of known natural and synthetic phosphorylated compounds.

The pH-optimum of the original fungal consensus phytase was around pH 6.0–6.5 (70 U/mg). By introduction of the Q50T mutation, the pH-optimum shifted, to pH 6.0 (130 U/mg), while the replacement by a leucine at the same position resulted in a maximum activity around pH 5.5 (212 U/mg). The exchange Q50G resulted in a pH-optimum of the activity above pH 6.0 (see FIG. 4). The exchange of tyrosine at position 51 with asparagine resulted in a relative increase of the activity below pH 5.0 (see FIG. 5). Especially by the Q50L mutation, the specificity for phytate of fungal consensus phytase was drastically increased (see FIG. 6).

The temperature optimum of fungal consensus phytase (70° C.) was 15–25° C. higher than the temperature optimum of the wild-type phytases (45–55° C.) which were used to calculate the consensus sequence (see Table 5 and FIG. 3).

TABLE 5

| phytase | temperature optimum | Tm[a] |
|---|---|---|
| Consensus phytase | 70° C. | 78.0° C. |
| A. niger NRRL3135 | 55° C. | 63.3° C. |
| A. fumigatus 13073 | 55° C. | 62.5° C. |
| A. terreus 9A-1 | 49° C. | 57.5° C. |
| A. terreus cbs | 45° C. | 58.5° C. |
| A. nidulans | 45° C. | 55.7° C. |
| M. thermophila | 55° C. | — |

Table 5: Temperature optimum and $T_m$-value of fungal consensus phytase and of the phytases from A. fumigatus, A. niger, A. nidulans, and M. thermophila. The temperature optima were taken from FIG. 3. [a] The $T_m$-values were determined by differential scanning calorimetry as described in Example 10 and shown in FIG. 7.

Example 10

Determination of the Melting point by Differential Scanning Calorimetry (DSC)

In order to determine the unfolding temperature of the fungal consensus phytases, differential scanning calorimetry was applied as previously published by Brugger et al. (1997). Solutions of 50–60 mg/ml homogeneous phytase were used for the tests. A constant heating rate of 10° C./min was applied up to 90° C.

Figure 7A:
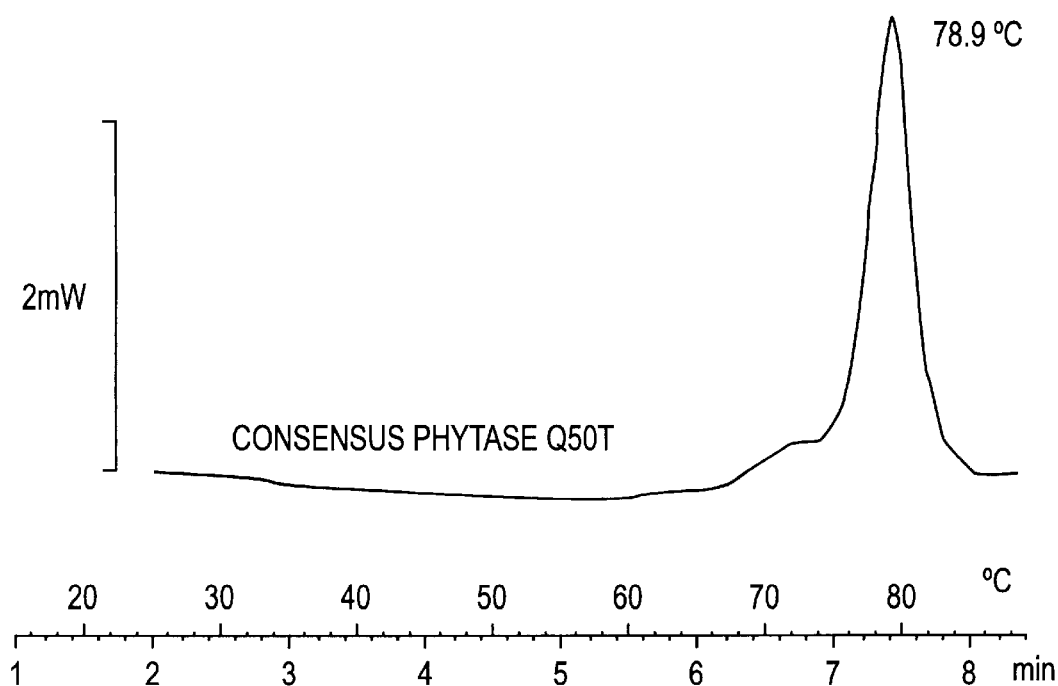
FIG. 7: Differential scanning calorimetry (DSC) of fungal consensus phytase and its mutant Q50T. The protein samples were concentrated to carry 50–60 mg/ml and extensively dialyzed against 10 mM sodium acetate, pH 5 A constant heating rate of 10° C./min was applied up to 90° C. DSC of consensus phytase Q50T (upper graph) yielded in a melting temperature of 78.9° C., which is nearly identical to the melting point of fungal consensus phytase (78.1° C., lower graph).
Figure 7B:
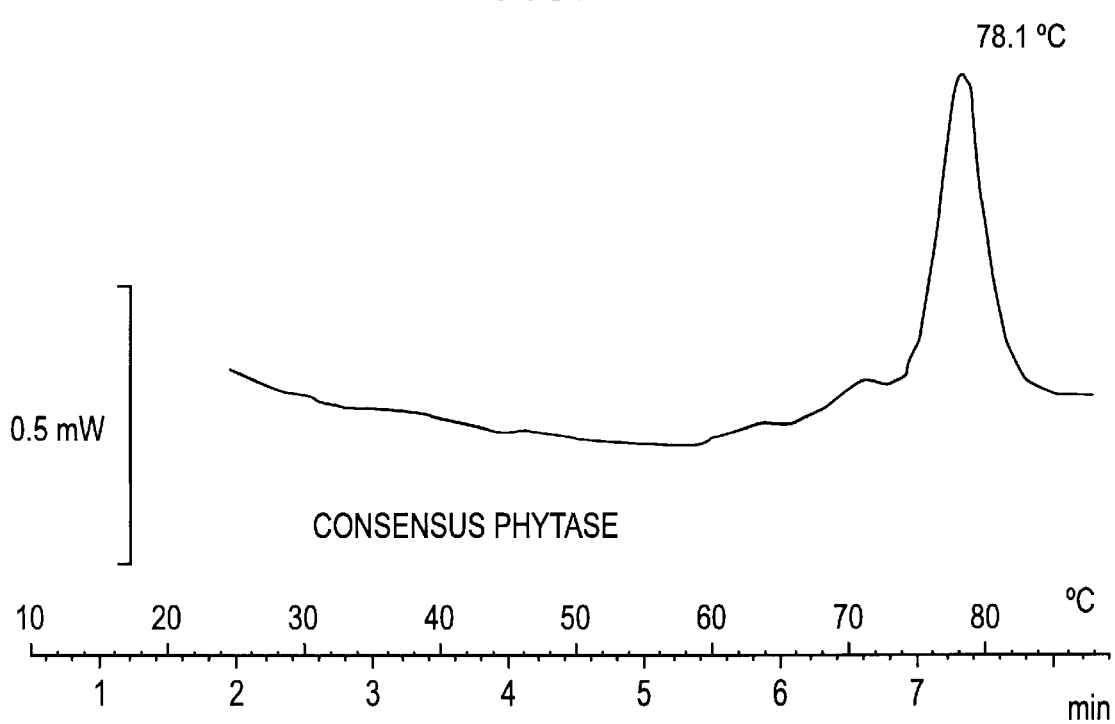

The determined melting points clearly show the strongly improved thermostability of the fungal consensus phytase in comparison to the wild-type phytases (see Table 5 and FIG. 7). FIG. 7 shows the melting profile of fungal consensus phytase and its mutant Q50T. Its common melting point was determined between 78 to 79° C.

What is claimed is:

1. A polynucleotide encoding a consensus protein of SEQ ID NO:2.

2. A polynucleotide encoding a consensus protein of SEQ ID NO:1.

3. A polynucleotide which encodes a consensus protein having the amino acid sequence of SEQ ID NO:2 except that Q at position 50 has been replaced by L, T, or G.

4. A polynucleotide which encodes a consensus protein having the amino acid sequence of SEQ ID NO:2 except that Q at position 50 has been replaced by T and Y at position 51 has been replaced by N.

5. A polynucleotide which encodes a consensus protein having the amino acid sequence of SEQ ID NO:2 except that Q at position 50 has been replaced by L and Y at position 51 has been replaced by N.

* * * * *

SEQUENCE LISTING

<160> NUMBER OF SEQ ID NOS: 20

<210> SEQ ID NO 1
<211> LENGTH: 441
<212> TYPE: PRT
<213> ORGANISM: Artificial Sequence
<220> FEATURE:
<223> OTHER INFORMATION: Description of Artificial Sequence:consensus
      sequence

<400> SEQUENCE: 1

```
Asn Ser His Ser Cys Asp Thr Val Asp Gly Gly Tyr Gln Cys Phe Pro
 1               5                  10                  15

Glu Ile Ser His Leu Trp Gly Gln Tyr Ser Pro Tyr Phe Ser Leu Glu
                20                  25                  30

Asp Glu Ser Ala Ile Ser Pro Asp Val Pro Asp Asp Cys Arg Val Thr
            35                  40                  45

Phe Val Gln Val Leu Ser Arg His Gly Ala Arg Tyr Pro Thr Ser Ser
        50                  55                  60

Lys Ser Lys Ala Tyr Ser Ala Leu Ile Glu Ala Ile Gln Lys Asn Ala
65                  70                  75                  80

Thr Ala Phe Lys Gly Lys Tyr Ala Phe Leu Lys Thr Tyr Asn Tyr Thr
                85                  90                  95

Leu Gly Ala Asp Asp Leu Thr Pro Phe Gly Glu Asn Gln Met Val Asn
            100                 105                 110

Ser Gly Ile Lys Phe Tyr Arg Arg Tyr Lys Ala Leu Ala Arg Lys Ile
        115                 120                 125

Val Pro Phe Ile Arg Ala Ser Gly Ser Asp Arg Val Ile Ala Ser Ala
    130                 135                 140

Glu Lys Phe Ile Glu Gly Phe Gln Ser Ala Lys Leu Ala Asp Pro Gly
145                 150                 155                 160

Ser Gln Pro His Gln Ala Ser Pro Val Ile Asp Val Ile Ile Pro Glu
                165                 170                 175

Gly Ser Gly Tyr Asn Asn Thr Leu Asp His Gly Thr Cys Thr Ala Phe
            180                 185                 190

Glu Asp Ser Glu Leu Gly Asp Asp Val Glu Ala Asn Phe Thr Ala Leu
        195                 200                 205
```

```
Phe Ala Pro Ala Ile Arg Ala Arg Leu Glu Ala Asp Leu Pro Gly Val
            210                 215                 220

Thr Leu Thr Asp Glu Asp Val Val Tyr Leu Met Asp Met Cys Pro Phe
225                 230                 235                 240

Glu Thr Val Ala Arg Thr Ser Asp Ala Thr Glu Leu Ser Pro Phe Cys
                    245                 250                 255

Ala Leu Phe Thr His Asp Glu Trp Arg Gln Tyr Asp Tyr Leu Gln Ser
            260                 265                 270

Leu Gly Lys Tyr Tyr Gly Tyr Gly Ala Gly Asn Pro Leu Gly Pro Ala
                275                 280                 285

Gln Gly Val Gly Phe Ala Asn Glu Leu Ile Ala Arg Leu Thr Arg Ser
            290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                    325                 330                 335

Asn Ser Met Ile Ser Ile Phe Phe Ala Leu Gly Leu Tyr Asn Gly Thr
            340                 345                 350

Ala Pro Leu Ser Thr Thr Ser Val Glu Ser Ile Glu Glu Thr Asp Gly
                355                 360                 365

Tyr Ser Ala Ser Trp Thr Val Pro Phe Gly Ala Arg Ala Tyr Val Glu
            370                 375                 380

Met Met Gln Cys Gln Ala Glu Lys Glu Pro Leu Val Arg Val Leu Val
385                 390                 395                 400

Asn Asp Arg Val Val Pro Leu His Gly Cys Ala Val Asp Lys Leu Gly
                    405                 410                 415

Arg Cys Lys Arg Asp Asp Phe Val Glu Gly Leu Ser Phe Ala Arg Ser
            420                 425                 430

Gly Gly Asn Trp Ala Glu Cys Phe Ala
            435                 440

<210> SEQ ID NO 2
<211> LENGTH: 467
<212> TYPE: PRT
<213> ORGANISM: Artificial Sequence
<220> FEATURE:
<223> OTHER INFORMATION: Description of Artificial Sequence:consensus
      sequence

<400> SEQUENCE: 2

Met Gly Val Phe Val Val Leu Leu Ser Ile Ala Thr Leu Phe Gly Ser
  1               5                  10                  15

Thr Ser Gly Thr Ala Leu Gly Pro Arg Gly Asn Ser His Ser Cys Asp
             20                  25                  30

Thr Val Asp Gly Gly Tyr Gln Cys Phe Pro Glu Ile Ser His Leu Trp
         35                  40                  45

Gly Gln Tyr Ser Pro Tyr Phe Ser Leu Glu Asp Glu Ser Ala Ile Ser
     50                  55                  60

Pro Asp Val Pro Asp Cys Arg Val Thr Phe Val Gln Val Leu Ser
 65                  70                  75                  80

Arg His Gly Ala Arg Tyr Pro Thr Ser Ser Lys Ser Lys Ala Tyr Ser
                 85                  90                  95

Ala Thr Tyr Asn Tyr Thr Leu Gly Ala Asp Asp Leu Thr Pro Phe Gly
            100                 105                 110

Glu Asn Gln Met Val Asn Ser Gly Ile Lys Phe Tyr Arg Arg Tyr Lys
        115                 120                 125
```

```
Ala Leu Ala Arg Lys Ile Val Pro Phe Ile Arg Ala Ser Gly Ser Asp
    130                 135                 140

Arg Val Ile Ala Ser Ala Glu Lys Phe Ile Glu Gly Phe Gln Ser Ala
145                 150                 155                 160

Lys Leu Ala Asp Pro Gly Ser Gln Pro His Gln Ala Ser Pro Val Ile
                165                 170                 175

Asp Leu Ile Glu Ala Ile Gln Lys Asn Ala Thr Ala Phe Lys Gly Lys
                180                 185                 190

Tyr Ala Phe Leu Lys Val Ile Ile Pro Glu Gly Ser Gly Tyr Asn Asn
                195                 200                 205

Thr Leu Asp His Gly Thr Cys Thr Ala Phe Glu Asp Ser Glu Leu Gly
    210                 215                 220

Asp Asp Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Glu Asp
                245                 250                 255

Val Val Tyr Leu Met Asp Met Cys Pro Phe Glu Thr Val Ala Arg Thr
                260                 265                 270

Ser Asp Ala Thr Glu Leu Ser Pro Phe Cys Ala Leu Phe Thr His Asp
    275                 280                 285

Glu Trp Arg Gln Tyr Asp Tyr Leu Gln Ser Leu Gly Lys Tyr Tyr Gly
    290                 295                 300

Tyr Gly Ala Gly Asn Pro Leu Gly Pro Ala Gln Gly Val Gly Phe Ala
305                 310                 315                 320

Asn Glu Leu Ile Ala Arg Leu Thr Arg Ser Pro Val Gln Asp His Thr
                325                 330                 335

Ser Thr Asn His Thr Leu Asp Ser Asn Pro Ala Thr Phe Pro Leu Asn
                340                 345                 350

Ala Thr Leu Tyr Ala Asp Phe Ser His Asp Asn Ser Met Ile Ser Ile
                355                 360                 365

Phe Phe Ala Leu Gly Leu Tyr Asn Gly Thr Ala Pro Leu Ser Thr Thr
    370                 375                 380

Ser Val Glu Ser Ile Glu Glu Thr Asp Gly Tyr Ser Ala Ser Trp Thr
385                 390                 395                 400

Val Pro Phe Gly Ala Arg Ala Tyr Val Glu Met Met Gln Cys Gln Ala
                405                 410                 415

Glu Lys Glu Pro Leu Val Arg Val Leu Val Asn Asp Arg Val Val Pro
                420                 425                 430

Leu His Gly Cys Ala Val Asp Lys Leu Gly Arg Cys Lys Arg Asp Asp
    435                 440                 445

Phe Val Glu Gly Leu Ser Phe Ala Arg Ser Gly Gly Asn Trp Ala Glu
    450                 455                 460

Cys Phe Ala
465

<210> SEQ ID NO 3
<211> LENGTH: 1426
<212> TYPE: DNA
<213> ORGANISM: Artificial Sequence
<220> FEATURE:
<223> OTHER INFORMATION: Description of Artificial Sequence:consensus
      sequence

<400> SEQUENCE: 3
tatatgaatt catgggcgtg ttcgtcgtgc tactgtccat tgccaccttg ttcggttcca      60
```

-continued

```
catccggtac cgccttgggt cctcgtggta attctcactc ttgtgacact gttgacggtg    120
gttaccaatg tttcccagaa atttctcact tgtggggtca atactctcca tacttctctt    180
tggaagacga atctgctatt tctccagacg ttccagacga ctgtagagtt actttcgttc    240
aagttttgtc tagacacggt gctagatacc caacttcttc taagtctaag gcttactctg    300
ctttgattga agctattcaa aagaacgcta ctgctttcaa gggtaagtac gctttcttga    360
agacttacaa ctacactttg ggtgctgacg acttgactcc attcggtgaa accaaatgg     420 ttaactctgg tattaagttc tacagaagat acaaggcttt ggctagaaag attgttccat    480
tcattagagc ttctggttct gacagagtta ttgcttctgc tgaaaagttc attgaaggtt    540
tccaatctgc taagttggct gacccaggtt ctcaaccaca ccaagcttct ccagttattg    600
acgttattat tccagaagga tccggttaca acaacacttt ggaccacggt acttgtactg    660
ctttcgaaga ctctgaattg ggtgacgacg ttgaagctaa cttcactgct tgttcgctc     720 cagctattag agctagattg gaagctgact tgccaggtgt tactttgact gacgaagacg    780
ttgtttactt gatggacatg tgtccattcg aaactgttgc tagaacttct gacgctactg    840
aattgtctcc attctgtgct ttgttcactc acgacgaatg gagacaatac gactacttgc    900
aatctttggg taagtactac ggttacggtg ctggtaaccc attgggtcca gctcaaggtg    960
ttggtttcgc taacgaattg attgctagat tgactagatc tccagttcaa gaccacactt    1020
ctactaacca cactttggac tctaacccag ctactttccc attgaacgct actttgtacg    1080
ctgacttctc tcacgacaac tctatgattt ctattttctt cgctttgggt ttgtacaacg    1140
gtactgctcc attgtctact acttctgttg aatctattga agaaactgac ggttactctg    1200
cttcttggac tgttccattc ggtgctagag cttacgttga aatgatgcaa tgtcaagctg    1260
aaaaggaacc attggttaga gttttggtta acgacagagt tgttccattg cacggttgtg    1320
ctgttgacaa gttgggtaga tgtaagagag acgacttcgt tgaaggtttg tctttcgcta    1380
gatctggtgg taactgggct gaatgtttcg cttaagaatt catata              1426
```

<210> SEQ ID NO 4
<211> LENGTH: 1426
<212> TYPE: DNA
<213> ORGANISM: Artificial Sequence
<220> FEATURE:
<223> OTHER INFORMATION: Description of Artificial Sequence:consensus sequence

<400> SEQUENCE: 4

```
atatacttaa gtacccgcac aagcagcacg atgacaggta acggtggaac aagccaaggt     60
gtaggccatg gcggaaccca ggagcaccat taagagtgag aacactgtga caactgccac    120
caatggttac aaagggtctt taagagtgaa cacccagt tatgagaggt atgaagagaa     180
accttctgct tagacgataa agaggtctgc aaggtctgct gacatctcaa tgaaagcaag    240
ttcaaaacag atctgtgcca cgatctatgg gttgaagaag attcagattc cgaatgagac    300
gaaactaact tcgataagtt ttcttgcgat gacgaaagtt cccattcatg cgaaagaact    360
tctgaatgtt gatgtgaaac ccacgactgc tgaactgagg taagccactt ttggtttacc    420
aattgagacc ataattcaag atgtcttcta tgttccgaaa ccgatctttc taacaaggta    480
agtaatctcg aagaccaaga ctgtctcaat aacgaagacg acttttcaag taacttccaa    540
aggttagacg attcaaccga ctgggtccaa gagttggtgt ggttcgaaga ggtcaataac    600
tgcaataata aggtcttcct aggccaatgt tgttgtgaaa cctggtgcca tgaacatgac    660
```

```
gaaagcttct gagacttaac ccactgctgc aacttcgatt gaagtgacga aacaagcgag    720
gtcgataatc tcgatctaac cttcgactga acggtccaca atgaaactga ctgcttctgc    780
aacaaatgaa ctacctgtac acaggtaagc tttgacaacg atcttgaaga ctgcgatgac    840
ttaacagagg taagacacga aacaagtgag tgctgcttac ctctgttatg ctgatgaacg    900
ttagaaaccc attcatgatg ccaatgccac gaccattggg taacccaggt cgagttccac    960
aaccaaagcg attgcttaac taacgatcta actgatctag aggtcaagtt ctggtgtgaa   1020
gatgattggt gtgaaacctg agattgggtc gatgaaaggg taacttgcga tgaaacatgc   1080
gactgaagag agtgctgttg agatactaaa gataaaagaa gcgaaaccca aacatgttgc   1140
catgacgagg taacagatga tgaagacaac ttagataact tctttgactg ccaatgagac   1200
gaagaacctg acaaggtaag ccacgatctc gaatgcaact ttactacgtt acagttcgac   1260
ttttccttgg taaccaatct caaaaccaat tgctgtctca acaaggtaac gtgccaacac   1320
gacaactgtt caacccatct acattctctc tgctgaagca acttccaaac agaaagcgat   1380
ctagaccacc attgacccga cttacaaagc gaattcttaa gtatat                  1426

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 5
tatatgaatt catgggcgtg ttcgtc                                           26

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 6
tgaaaagttc attgaaggtt tc                                               22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 7
tgaaaagttc attgaaggtt tc                                               22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 8
tgaaaagttc attgaaggtt tc                                               22

<210> SEQ ID NO 9
<211> LENGTH: 33
<212> TYPE: DNA
```

```
<213> ORGANISM: Artificial Sequence
<220> FEATURE:
<223> OTHER INFORMATION: Description of Artificial Sequence:primer

<400> SEQUENCE: 9
tatatcatga gcgtgttcgt cgtgctactg ttc                          33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 10
acccgactta caaagcgaat tctatagata tat                          33

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 11
cacttgtggg gtttgtacag tccatacttc tc                           32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 12
gagaagtatg gactgtacaa accccacaag tg                           32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 13
cacttgtggg gtacctactc tccatacttc tc                           32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 14
gagaagtatg gagagtaggt accccacaag tg                           32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 15
cacttgtggg gtggttactc tccatacttc tc                           32
```

```
<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 16
gagaagtatg gagagtaacc accccacaag tg                                    32

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 17
cacttgtggg gtaccaactc tccatacttc tc                                    32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 18
gagaagtatg gagagttggt accccacaag tg                                    32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 19
cacttgtggg gtctcaactc tccatacttc tc                                    32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 20
gagaagtatg gagagttgag accccacaag tg                                    32
```